US012755841B2

(12) United States Patent
Zhou et al.

(10) Patent No.: US 12,755,841 B2
(45) Date of Patent: Oct. 6, 2026

(54) # MULTI-SITE CROSS-ORGAN CALIBRATED DEEP LEARNING (MUSCID) METHOD AND APPARATUS

(71) Applicants: Case Western Reserve University, Cleveland, OH (US); Emory University, Atlanta, GA (US); Southern Sun Pathology, Thornleigh (AU); Kantonsspital Aarau AG, Aarau (CH)

(72) Inventors: Yufei Zhou, Cleveland, OH (US); Can Koyuncu, Cleveland, OH (US); Cheng Lu, Cleveland, OH (US); Rainer Grobholz, Rupperswil (CH); Ian Katz, Thornleigh (AU); Anant Madabhushi, Decatur, GA (US); Andrew Janowczyk, East Meadow, NY (US)

(73) Assignees: Case Western Reserve University, Cleveland, OH (US); Emory University, Atlanta, GA (US); Kantonsspital Aarau AG, Aarau (CH); Southern Sun Pathology, Thornleigh (AU)

( * ) Notice: Subject to any disclaimer, the term of this patent is extended or adjusted under 35 U.S.C. 154(b) by 347 days.

(21) Appl. No.: 18/513,756

(22) Filed: Nov. 20, 2023

(65) Prior Publication Data

US 2024/0420841 A1 Dec. 19, 2024

Related U.S. Application Data

(60) Provisional application No. 63/508,283, filed on Jun. 15, 2023.

(51) Int. Cl.
*G16H 50/20* (2018.01)
*G16H 30/40* (2018.01)
*G16H 50/70* (2018.01)

(52) U.S. Cl.
CPC ............ *G16H 50/20* (2018.01); *G16H 30/40* (2018.01); *G16H 50/70* (2018.01)

(58) Field of Classification Search
None
See application file for complete search history.

(56) References Cited

U.S. PATENT DOCUMENTS

2023/0162023 A1 * 5/2023 Koike Akino ....... G06N 3/0455 706/25
2025/0064406 A1 * 2/2025 Park ......................... G06N 3/08
2025/0079016 A1 * 3/2025 Vatanparvar ........... G06V 10/82

* cited by examiner

*Primary Examiner* — Dov Popovici
(74) *Attorney, Agent, or Firm* — Eschweiler & Potashnik, LLC

(57) ABSTRACT

The present disclosure, in some embodiments, relates to a method of mitigating domain shift. The method includes accessing a first imaging data set having one or more first images from a first site and accessing a second imaging data set having one or more second images from a second site. The one or more first images respectively include a first on-target region. The one or more second images respectively include a second off-target region. The first on-target region is modified using the second off-target region to generate a calibrated first on-target region. The calibrated first on-target region has a first domain shift with respect to the second off-target region and the first on-target region has a second domain shift with respect to the first on-target region. The first domain shift is smaller than the second domain shift.

20 Claims, 19 Drawing Sheets
(10 of 19 Drawing Sheet(s) Filed in Color)

900

| | p-value | Red | Green | Blue |
|---|---|---|---|---|
| $A_S$ vs. $B_S$ | $3 \times 10^{-105}$ | 0.02 | 0.09 | 0.08 |
| $B_L$ vs. $B_S$ | $8 \times 10^{-218}$ | 0.03 | 0.04 | 0.02 |

902 904

Fig. 9A

906

908 910 912 914

| | | $A_S$ | $A_S^L$ | $B_S$ | $A_S^S$ |
|---|---|---|---|---|---|
| Benign | R | 0.86 ± 0.05 | 0.86 ± 0.03 | 0.87 ± 0.03 | 0.87 ± 0.04 |
| | G | 0.69 ± 0.08 | 0.76 ± 0.05 | 0.77 ± 0.05 | 0.75 ± 0.07 |
| | B | 0.81 ± 0.04 | 0.89 ± 0.02 | 0.86 ± 0.02 | 0.88 ± 0.03 |
| BCC | R | 0.73 ± 0.06 | 0.78 ± 0.02 | 0.84 ± 0.04 | 0.74 ± 0.06 |
| | G | 0.57 ± 0.08 | 0.67 ± 0.04 | 0.74 ± 0.06 | 0.61 ± 0.07 |
| | B | 0.74 ± 0.04 | 0.85 ± 0.02 | 0.87 ± 0.02 | 0.83 ± 0.04 |
| SCC-In Situ | R | 0.79 ± 0.04 | 0.82 ± 0.03 | 0.82 ± 0.05 | 0.79 ± 0.05 |
| | G | 0.61 ± 0.08 | 0.71 ± 0.05 | 0.71 ± 0.07 | 0.63 ± 0.08 |
| | B | 0.77 ± 0.04 | 0.87 ± 0.02 | 0.86 ± 0.03 | 0.83 ± 0.04 |
| SCC-Invasive | R | 0.85 ± 0.04 | 0.84 ± 0.03 | 0.83 ± 0.03 | 0.86 ± 0.03 |
| | G | 0.65 ± 0.51 | 0.74 ± 0.04 | 0.70 ± 0.05 | 0.72 ± 0.04 |
| | B | 0.80 ± 0.02 | 0.88 ± 0.01 | 0.85 ± 0.03 | 0.87 ± 0.01 |

Fig. 9B

MULTI-SITE CROSS-ORGAN CALIBRATED DEEP LEARNING (MUSCID) METHOD AND APPARATUS

CROSS REFERENCE TO RELATED APPLICATIONS

This application claims the benefit of priority from U.S. Provisional Patent Application No. 63/508,283 filed Jun. 15, 2023 and entitled "MULTI-SITE CROSS-ORGAN CALIBRATED DEEP LEARNING (MUSCID): AUTOMATED DIAGNOSIS OF NON-MELANOMA SKIN CANCER", the contents of which are incorporated herein by reference in their entirety.

FEDERAL FUNDING NOTICE

This invention was made with government support under CA239055, CA248226, CA254566, HL151277, EB028736, RR012463, CA208236, CA216579, CA220581, CA199374, and CA202752 awarded by the National Institutes of Health; W81XWH-18-1-0404, W81XWH-19-1-0668, W81XWH-15-1-0558, W81XWH-20-1-0851, and W81XWH-18-1-0440 awarded by the Department of Defense, and IBX004121A awarded by the Veterans Administration. The government has certain rights in the invention.

BACKGROUND

Batch effects are technical sources of variation (e.g., non-biological factors) that are present between different groups or batches of data. Batch effects may be generated within a set of data due to differences in preparation of samples within different batches, differences in a type or model of a machine used to collect the data of the different batches, or even by different technicians that collect the data of the different batches.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

FIG. 9A illustrates a table showing exemplary comparisons between RGB (Red/Green/Blue) values of different uncalibrated NMSC images.

FIG. 9B illustrates a table showing exemplary comparisons between RGB values of calibrated and uncalibrated images for different NMSC classifications.

DETAILED DESCRIPTION

Figure 1:
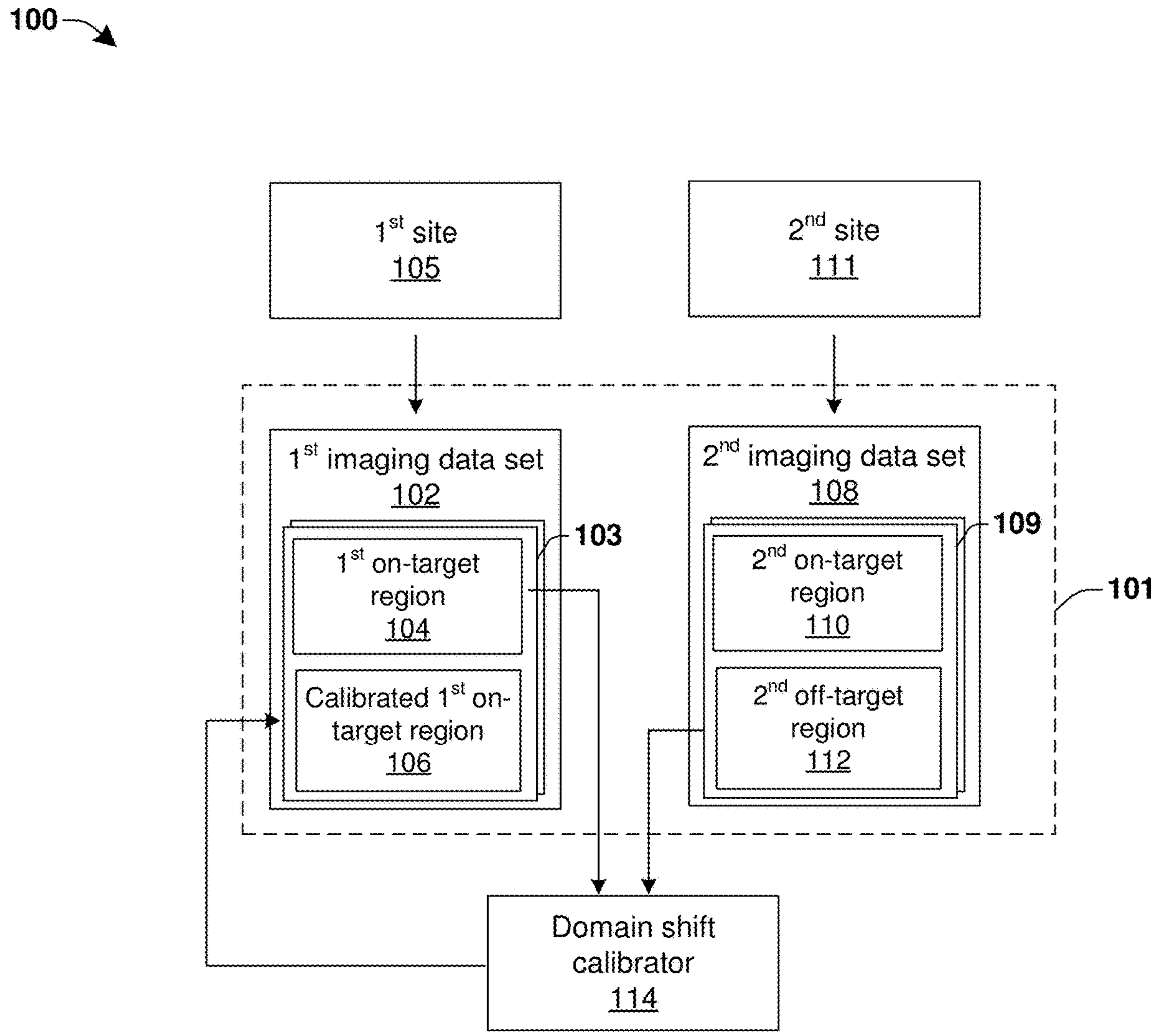
FIG. 1 illustrates a block diagram of a domain shift mitigation apparatus configured to reduce domain shift batch effects in an imaging data set.

The description herein is made with reference to the drawings, wherein like reference numerals are generally utilized to refer to like elements throughout, and wherein the various structures are not necessarily drawn to scale. In the following description, for purposes of explanation, numerous specific details are set forth in order to facilitate understanding. It may be evident, however, to one of ordinary skill in the art, that one or more aspects described herein may be practiced with a lesser degree of these specific details. In other instances, known structures and devices are shown in block diagram form to facilitate understanding.

Globally, there has been a significant increase in non-melanoma skin cancer (NMSC) incidence, especially in Caucasians. Seventy-five percent of NMSC cases correspond to basal cell carcinoma (BCC) which has a low risk of mortality (<0.1%). The majority of remaining NMSC cases are squamous cell carcinomas (SCC), which when left untreated are far more likely to metastasize to other organs (0.3-3.7%), leading to an increased risk of mortality. As such, an accurate differential diagnosis between BCC and SCC is important. Furthermore, SCC can be either SCC-In Situ (e.g., Bowen disease) or SCC-Invasive. While SCC-In Situ is a superficial form of SCC, it has relatively high risk (3%-5%) of progression to SCC-Invasive. Since approximately 1.1% of women and 2.4% of men with SCC-Invasive eventually develop tumor metastases, accurate diagnosis and close monitoring of SCC subtypes is warranted.

The diagnosis of NMSC may be performed by pathologists identifying characteristic histological features of each NMSC subtype from hematoxylin and eosin (H&E) stained tissue specimens. BCC is a type of basaloid epithelial tumor arising from the basal layer of the epidermis. The basaloid cells form a regular palisade at the periphery of the tumor nest while their distribution in the middle of the nest is chaotic. On the other hand, SCC is often characterized by relatively large polyhedral cells with abundant, glassy eosinophilic cytoplasm with copious keratin formation. While the consensus among dermatopathologists tends to be high in identifying BCC (>95%), concordance is relatively lower for SCC (77%). In addition, it may be non-trivial to distinguish between SCC-In Situ and SCC-Invasive.

Deep learning (DL) strategies are well suited for classification subtyping and can enable improved identification of benign tissue, BCC, and SCC. Unfortunately, variations of pre-analytical variabilities in slide preparation (e.g., staining protocol, slide scanner, tissue thickness) can degrade DL performance. For example, similar BCC cases from two different sites may suffer from visually perceivable differences in terms of image hue/saturation/value (HSV), red/blue/green (RGB), contrast, and brightness values. These variabilities contribute to a phenomenon known as "domain shift," wherein testing data and training data lie on different underlying distributions. Domain shift heavily impacts performance of a trained DL model operated upon images from a new site, where variations of pre-analytical variabilities are often most significant.

To avoid such performance degradation, training images and testing images may be calibrated to more closely resemble one another to help ameliorate pre-analytic differences using post-image acquisition processing steps (e.g., a stain color of a testing image may be modified to more closely resemble a stain color of a training image to mitigate stain differences between the images). However, current approaches for addressing domain shift using post-image acquisition processing steps suffer from a number of potential issues.

For example, aligning testing data to training data can introduce artifacts including blur, checkerboard artifacts, and/or texture distortions into the testing data. These artifacts may have a negative impact on the performance of DL image analysis pipelines. To mitigate artifact introduction on testing data, training data can be calibrated to more closely resemble the testing data so as to form a site-specific DL model. However, calibrating an organ shown in training data to resemble a same type of organ in testing data can introduce data leakage (e.g., imparting information from testing data into training data), thereby violating a strict separation between training data and testing data. For example, a Generative Adversarial Network (GAN) could impart specific knowledge from testing images (e.g., that BCC cells from an external test site are slightly larger due to microns per pixel differences in the scanner) into training images (e.g., by modifying training image BCC cell size). Moreover, it remains difficult to quantify an extent and/or impact of such data leakage.

The present disclosure relates to a method and apparatus for mitigating domain shift batch effects between images having different data acquisition attributes (e.g., due to different acquisition sites) using images of both an on-target organ (e.g., an organ that is used in subsequent machine learning analysis) and an off-target organ (e.g., an organ that is not used in subsequent machine learning analysis). In some embodiments, the method calibrates training images of an on-target organ, to more closely resemble testing image of an on-target organ, by using a testing image of an off-target organ generated at a same site as the testing image of the on-target organ. Because the on-target and off-target organs within testing images are subjected to a same set of pre-analytical sources of variance, the testing image of the off-target organ can be used to reduce a domain shift between the on-target organs within the training and testing images. Furthermore, accounting for domain shift using an off-target organ guards against potential data leakage during calibration, thereby improving a performance of downstream analysis.

FIG. 1 illustrates a block diagram of a domain shift mitigation apparatus 100 configured to reduce domain shift batch effects in an imaging data set.

The domain shift mitigation apparatus 100 comprises a memory 101 configured to store a first imaging data set 102 and a second imaging data set 108. The first imaging data set 102 comprises one or more first images 103 that were generated at a first site 105 and the second imaging data set 108 comprises one or more second images 109 that were generated at a second site 111. In some embodiments, the first site 105 is at a first geographic location and the second site 111 is at a second geographic location that is different than the first geographic location. For example, the first site 105 may comprise a first hospital and the second site 111 may comprise a second hospital. The first site 105 and the second site 111 may have different tools (e.g., slide scanners) and/or procedures (e.g., staining procedures) that result in batch effects and/or domains shifts between the one or more first images 103 and the one or more second images 109. For example, the one or more first images 103 and the one or more second images 109 may have visually perceivable differences in terms of image hue/saturation/value (HSV), red/blue/green (RGB), contrast, brightness values, and/or the like.

The one or more first images 103 comprise a first on-target region 106. The one or more second images 109 comprise a second on-target region 110 and a second off-target region 112. In some embodiments, the first on-target region 106 is a first on-target organ (e.g., an organ that is used in subsequent machine learning analysis), the second on-target region 110 is a second on-target organ, and the second off-target region 112 is a second off-target organ (e.g., an organ that is not used in subsequent machine learning analysis).

A domain shift calibrator 114 is configured to access the first on-target region 104 from the first imaging data set 102 and the second off-target region 112 from the second imaging data set 108. The domain shift calibrator 114 is configured to use the second off-target region 112 to modify the first on-target region 104 and generate a calibrated first on-target region 106 that has similar visual characteristics to the second off-target region 112. In some embodiments, the domain shift calibrator 114 may be configured to generate a domain shift correction factor from the second off-target region 112. The domain shift correction factor is configured to mitigate a domain shift between the first on-target region 104 and the second off-target region 112. The domain shift calibrator 114 is further configured to apply the domain shift correction factor to the first on-target region 106 to generate the calibrated first on-target region 106.

It has been appreciated that pre-analytic variables imparted into images formed at a same site are sufficiently similar between regions (e.g., organs), such that images from the second off-target region 112 can be used to generate the calibrated first on-target region 106. Therefore, a cross-organ calibration process can be used to mitigate domain shifts between on-target regions within images from the first site 105 and the second site 111. Furthermore, generating the calibrated first on-target region 106 using the second off-target region 112 guards against potential data leakage (e.g., imparting information only available in testing data on training data) during calibration, thereby improving a performance of the domain shift mitigation apparatus 100.

Figure 2A:
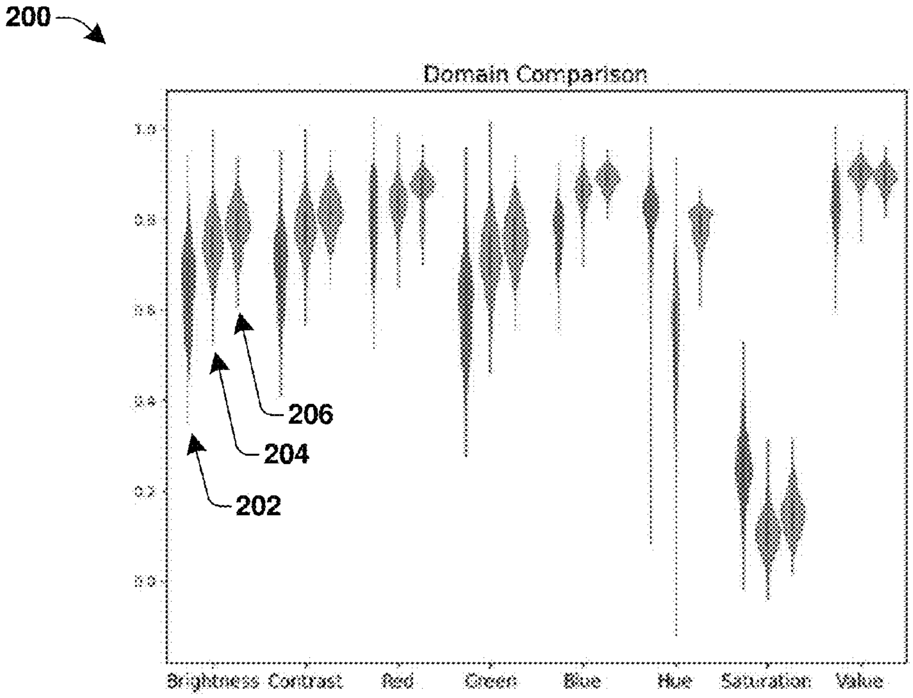
FIG. 2A illustrates a graph showing violin plots of inter-site domain shifts between a same type of organ at different sites and between different types of organs at a same site.

FIG. 2A illustrates a graph 200 showing violin plots illustrating inter-site domain shifts between a same type of organ at different sites and between different types of organs at a same site.

The graph 200 shows violin plots with values of brightness (e.g., mean intensity of each color channel), contrast, hue/saturation/value (HSV), and red/green/blue (RGB) for different organs and sites. The violin plots correspond to a first organ 204 (e.g., skin) from a first site, a second organ 206 (e.g., lung) from the first site, and a first organ 202 (e.g., skin) from a second site. A domain shift between the first organ 204 and the second organ 206 from the first site is smaller than a domain shift between the first organ 204 (e.g., skin) from the first site and the first organ 202 (e.g., skin) from the second site. This suggest that the use of different organs as calibration templates (e.g., the use of lung data for skin data calibration) in the disclosed cross-organ calibration approach is feasible.

Figure 2B:
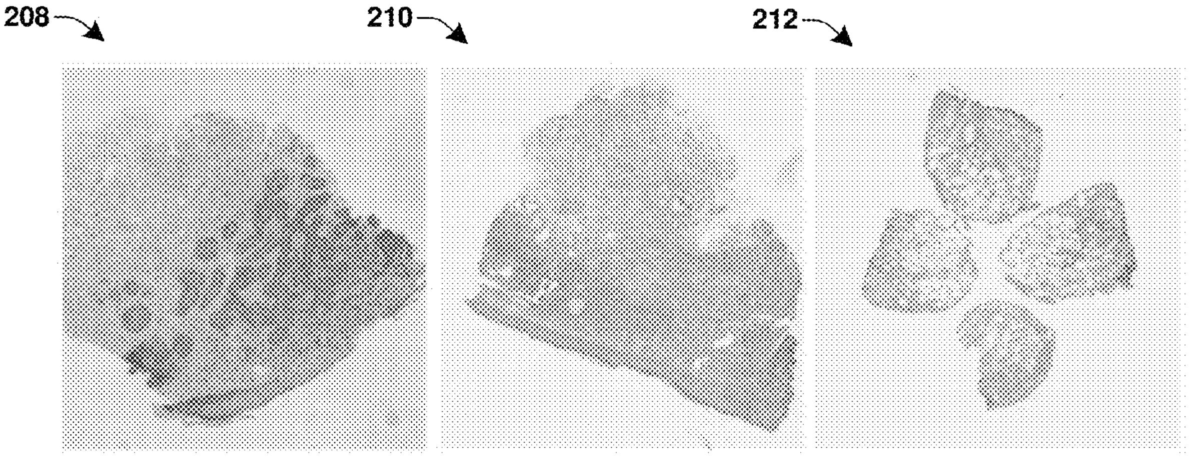
FIG. 2B illustrates images showing tissue samples of a same type of organ at different sites and of different types of organs at a same site.

FIG. 2B illustrates images 208-212 showing tissue samples of a same type of organ at different sites and different types of organs at a same site.

A first image 208 shows a first tissue sample from a first organ (e.g., skin) from a first site. A second image 210 shows a second tissue sample from a first organ (e.g., skin) from a second site. A third image 212 shows a third tissue sample from a second organ (e.g., lung) from the second site. Comparison of the first image 208 and the second image 210 shows that there are significant differences in visual appearance (e.g., image hue/saturation/value (HSV), red/blue/green (RGB), contrast, and brightness values) between the first organ from the first site and the second organ from the second site.

Comparison of the second image 210 and the third image 212 shows that the color of the second image 210 is similar in visual appearance to the third image 212. The similarities in visual appearance between the second image 210 and the third image 212 are likely due to similar variables associated with laboratory equipment (e.g., microtome, scanner, stainer) and/or biochemical properties (e.g., temperature, humidity, stain) of the second site. This further supports that the use of different organs as calibration templates in the disclosed cross-organ calibration approach is feasible.

Figure 3:
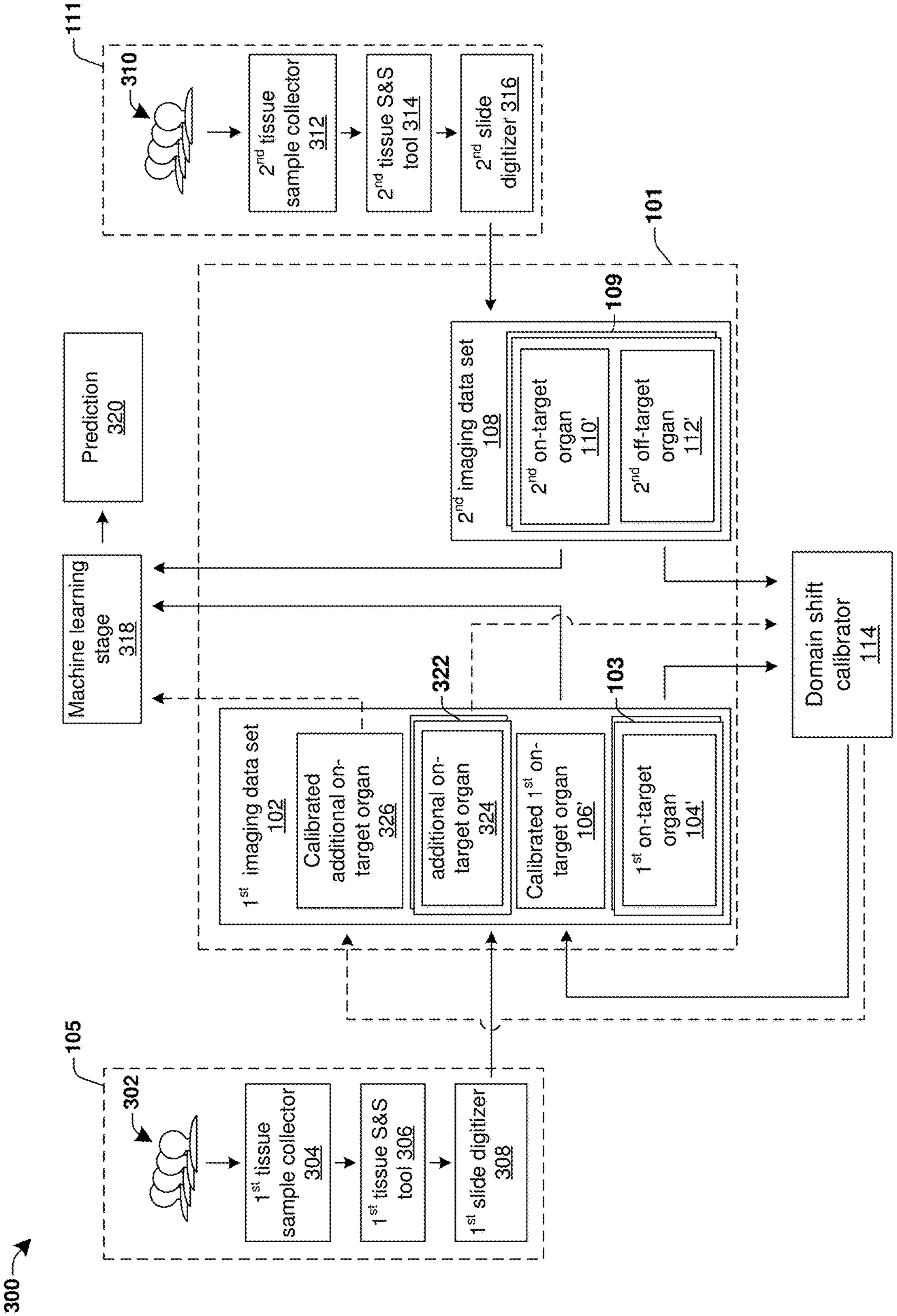
FIG. 3 illustrates a block diagram corresponding to some embodiments of a multi-site cross-organ calibrated machine learning system comprising a domain shift mitigation apparatus configured to reduce domain shift in an imaging data set.

FIG. 3 illustrates a block diagram corresponding to some embodiments of a multi-site cross-organ calibrated machine learning system 300 comprising a domain shift mitigation apparatus configured to reduce domain shift in an imaging data set.

The multi-site cross-organ calibrated machine learning system 300 comprises a memory 101 configured to store a first imaging data set 102 comprising one or more first images 103 (e.g., one or more whole slide images (WSIs), patches of a WSI, or the like) from a first site 105 and a second imaging data set 108 comprising one or more second images 109 (e.g., one or more WSIs, patches of a WSI, or the like) from a second site 111. In some embodiments, the memory 101 may comprise electronic memory (e.g., solid state memory, SRAM (static random-access memory), DRAM (dynamic random-access memory), and/or the like).

The one or more first images 103 respectively comprise a first on-target organ 104' that includes at least some tissue from an on-target organ imaged at the first site 105. The one or more second images 109 respectively comprise a second on-target organ 110' and a second off-target organ 112'. The second on-target organ 110' includes at least some tissue from an on-target organ imaged at the second site, while the second off-target organ 112' includes at least some tissue from an off-target organ imaged at the second site.

In some embodiments, the one or more first images 103 may comprise training data and the one or more second images 109 may comprise testing data. The training data may be used to train a downstream machine learning stage and/or model (e.g., machine learning algorithm), while the testing data may be used to validate the training of the machine learning model. In such embodiments, the disclosed multi-site cross-organ calibrated machine learning system 300 is able to guard against the introduction of data leakage during calibration. Furthermore, by only modifying the first imaging data set 102 (e.g., training data), the introduction of artifacts (e.g., blur, checkboard) into the second imaging data set 108 (e.g., testing data) is minimized, ensuring high fidelity unaltered input data to a downstream machine learning model. In other embodiments, the one or more first images 103 may comprise testing data and the one or more second images 109 may comprise training data. In yet other embodiments, the one or more first images 103 may be broken into groups that are configured to act as training and testing data.

In some embodiments, the first site 105 may comprise a first tissue sample collector 304 (e.g., a cannular, forceps, needle, punch, scalpel, or the like) configured to collect tissue samples from one or more first patients 302. In some embodiments, the one or more first patients 302 may comprise cancer patients. The cancer patients may have skin cancer, lung cancer, liver cancer, prostate cancer, or the like. The one or more tissue samples may be provided to a first tissue sectioning and staining tool 306 configured to slice the one or more tissue samples into thin slices that are placed on transparent slides (e.g., glass slides) to generate biopsy slides. The tissue on the biopsy slides is then stained by applying a dye. In some embodiments, the biopsy slides may comprise H&E (Hematoxylin and Eosin) stained slides, PAS (Periodic Acid Schiff) stained slides, or the like. A first slide digitizer 308 (e.g., scanner) is configured to convert the biopsy slides to digitized images (e.g., WSIs). In some embodiments, the first slide digitizer 308 may comprise an image sensor (e.g., a photodiode, CMOS image sensor, or the like) that is configured to generate a digital image comprising a whole slide image (WSI).

The second site 111 may comprise a second tissue sample collector 312 configured to collect tissue samples from one or more second patients 310. In some embodiments, the one or more second patients 310 may comprise cancer patients having skin cancer, lung cancer, liver cancer, prostate cancer, or the like. The one or more tissue samples may be provided to a second tissue sectioning and staining tool 314 configured to generate biopsy slides (e.g., H&E stained slides). A second slide digitizer 316 (e.g., scanner) is configured to convert the biopsy slides to digitized images (e.g., WSIs). In some embodiments, the first slide digitizer 308 and/or the first tissue sectioning and staining tool 306 may be different than the second slide digitizer 316 and/or the second tissue sectioning and staining tool 314, causing the one or more first images 103 and the one or more second images 109 to have visually perceivable differences in terms of HSV, RGB, contrast, brightness values, and/or the like.

A domain shift calibrator 114 is configured to access the first on-target organ 104' and the second off-target organ 112'. The domain shift calibrator 114 is configured to modify an appearance of the first on-target organ 104' based upon the second off-target organ 112' to generate a calibrated first on-target organ 106' that has similar visual characteristics as the second on-target organ 110'. In some embodiments, the domain shift calibrator 114 may comprise a trained general adversarial network (GAN) run on one or more processors (e.g., a central processing unit including one or more transistor devices configured to operate computer code to achieve a result, a microcontroller, or the like). In some embodiments, the domain shift calibrator 114 is configured to use the second off-target organ 112' to determine a domain shift correction factor that is configured to mitigate a difference in domain shift between the first on-target organ 104' and the second on-target organ 110'. The domain shift calibrator 114 is further configured to apply the domain shift correction factor to the first on-target organ 104' to generate the calibrated first on-target organ 106'.

A machine learning stage 318 (e.g., including a machine learning model) is configured to access the calibrated first on-target organ 106' and/or the second on-target organ 110'. In some embodiments, the calibrated first on-target organ 106' may be used to train the machine learning stage 318 to generate a medical prediction 320 concerning a patient (e.g., a classification of tissue as cancerous or benign, a classification of tissue as a sub-type of a cancer, or the like). In some embodiments, a first subset of data corresponding to the calibrated first on-target organ 106' is utilized to train the machine learning mode, while a disjoint subset of the calibrated first on-target organ 106' is used to validate training of the machine learning stage 318. In other embodiments, subsets of the second on-target organ 110' may be used to train and validate the machine learning stage 318. In some embodiments, the machine learning stage 318 may comprise a deep learning model. In some embodiments, the machine learning stage 318 may comprise a regression model, a Cox Hazard regression model, a support vector machine, a linear discriminant analysis (LDA) classifier, a naïve Bayes classifier, or the like, run on one more processors.

Once the machine learning stage 318 has been trained, the machine learning stage 318 can be operated upon a calibrated additional on-target image (e.g., an additional on-target region and/or organ) generated at the first site 105 and calibrated by the domain shift calibrator 114 and/or upon a second on-target organ 110' without calibration. For example, in some embodiments, the memory 101 may be further configured to store one or more additional images 322 of an additional patient (e.g., that are taken during a medical appointment). The one or more additional images 322 may be generated at the first site 105. The one or more additional images 322 comprise an additional on-target organ 324 (e.g., including at least some tissue from an on-target organ). The domain shift calibrator 114 may be configured to modify an appearance of the additional on-target organ 324 to generate a calibrated additional on-target organ 326 that has similar visual characteristics as the second on-target organ 110'. Because the calibrated additional on-target organ 326 has similar visual characteristics as the second on-target organ 110', a domain shift of the calibrated additional on-target organ 326 is small and the machine learning stage 318 is able to generate the medical prediction 320 to be accurate for the additional patient.

It has been appreciated that when operating on data from different sites, deep learning models are typically unable to accurately distinguish between different subtypes of cancer (e.g., to distinguish SCC-In Situ from SCC-Invasive) due to domain shift batch effects. However, because the domain shift calibrator 114 has reduced a domain shift between the first on-target organ 104' and the second on-target organ 110', the machine learning stage 318 is able to improve an accuracy of the machine learning stage 318 in tissue classification across different sites.

In some embodiments, the domain shift calibrator 114 may be configured to perform a new cross-organ calibration when data from a new site is received. For example, a third imaging data set (not shown) may be received from a third site and have one or more third images comprising a third on-target organ (e.g., including at least some tissue from an on-target organ imaged at the third site). The domain shift calibrator 114 may be configured to modify an appearance of the third on-target organ based upon the second off-target organ 112' to generate a calibrated third on-target organ that has similar visual characteristics as the second on-target organ 110'. It will be appreciated that using the domain shift calibrator 114 to account for a domain shift in the third imaging data set allows for a machine learning stage and/or model that was trained on the first imaging data set 102 and the second imaging data set 108 to be used on the third imaging data set without having to retrain the machine learning stage and/or model, thereby saving training time. Alternatively, the machine learning stage and/or model can be re-trained on the on-target images from the second imaging data set and calibrated on-target images from the third imaging data set.

Figure 4:
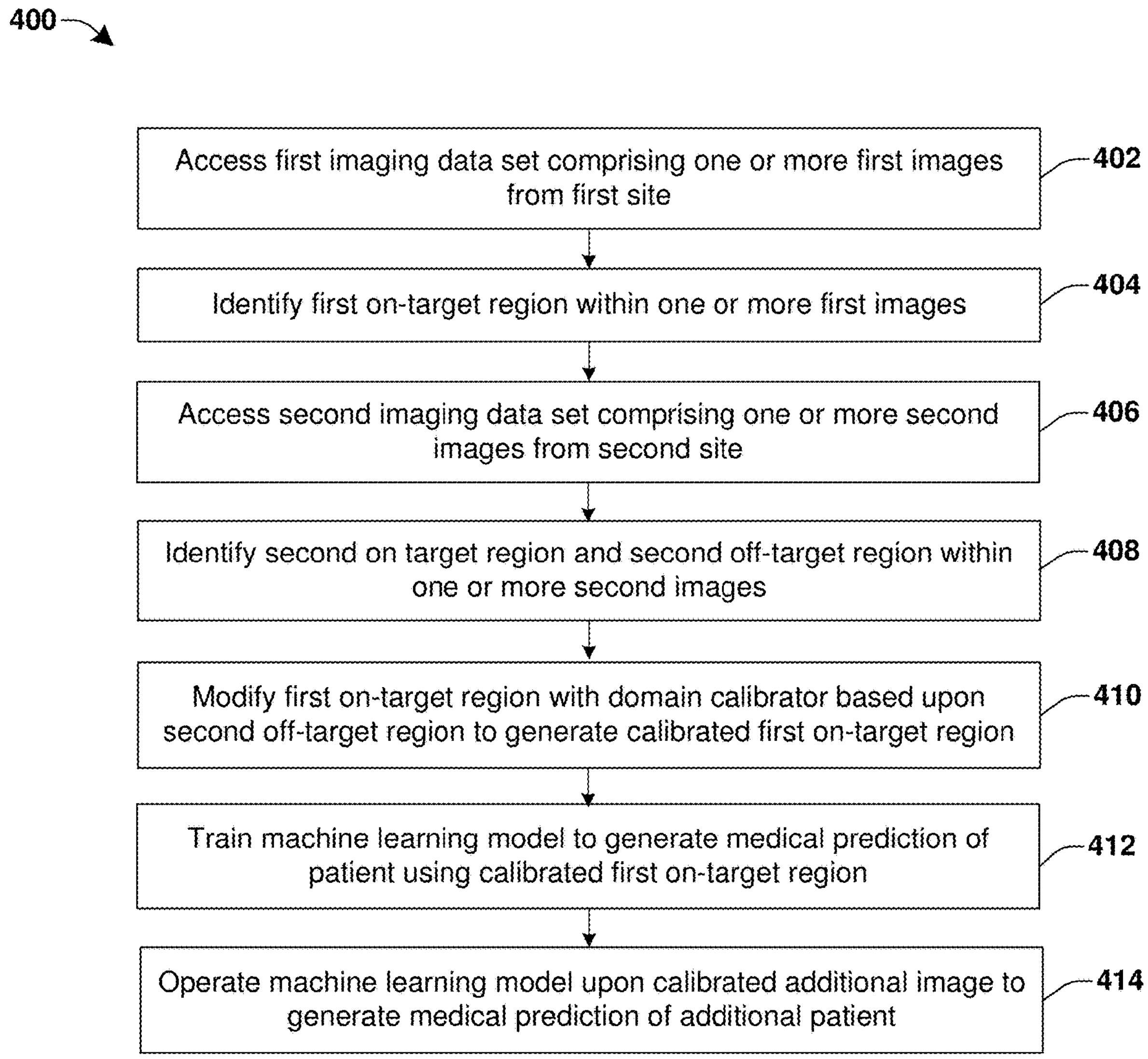
FIG. 4 illustrates a flow diagram of some embodiments of a method of mitigating domain shift in an imaging data set.

FIG. 4 illustrates a flow diagram of some embodiments of a method 400 of mitigating domain shift in an imaging data set.

While the disclosed methods (e.g., methods 400 and 600) are illustrated and described herein as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the description herein. Further, one or more of the acts depicted herein may be carried out in one or more separate acts and/or phases.

At act 402, a first imaging data set comprising one or more first images from a first site is accessed.

At act 404, a first on-target region is identified within the one or more first images. The first on-target region is a region comprising tissue (e.g., from a first type of organ) that is used in subsequent machine learning analysis.

At act 406, a second imaging data set comprising one or more second images from a second site is accessed.

At act 408, a second off-target region is identified within the one or more second images. The second off-target region is a region comprising tissue (e.g., from a second type of organ that is different than the first type of organ) that is not used in subsequent machine learning analysis.

At act 410, the first on-target region is modified by a domain calibrator based upon the second off-target region to generate a calibrated first on-target region.

At act 412, a machine learning stage is trained using the calibrated first on-target region to generate a medical prediction of a patient. By using the second off-target organ to calibrate the first on-target organ (i.e., calibrating in a cross-organ fashion), pre-analytical variables are exposed for learning while data leakage from the first imaging data set and the second imaging data set is largely avoided. This ensures a genuine independent evaluation of the machine learning stage (e.g., a deep learning model) between different sites.

At act 414, the machine learning stage is operated upon an additional image to generate a medical prediction of the additional patient. In some embodiments, the additional image may comprise a calibrated additional image generated at the first site and calibrated by the domain calibrator. In other embodiments, the additional image may comprise an image generated at the second site and not calibrated by the domain calibrator.

It will be appreciated that acts 402-408 may be performed every time that data from a new site is received. For example, in some embodiments, acts 402-408 may be performed in a first sequence with data from a first site and from a second site and acts 402-408 may be performed in a second sequence with data from a third site and from the second site. During the first sequence, an image from the first site is calibrated to look like an image from the second site, so that the image from the first site may be properly classified by the trained machine learning stage. During the second sequence, an image from the third site is calibrated to look like the image from the second site, so that the image from the third site may be properly classified by the trained machine learning stage.

It will be appreciated that the disclosed methods and/or block diagrams may be implemented as computer-executable instructions, in some embodiments. Thus, in one example, a computer-readable storage device (e.g., a non-transitory computer-readable medium) may store computer executable instructions that if executed by a machine (e.g., computer, processor) cause the machine to perform the disclosed methods and/or block diagrams. While executable instructions associated with the disclosed methods and/or block diagrams are described as being stored on a computer-readable storage device, it is to be appreciated that executable instructions associated with other example disclosed methods and/or block diagrams described or claimed herein may also be stored on a computer-readable storage device. In some embodiments, the computer-executable instructions may be implemented within a software package, so as to allow a health care professional to utilize the disclosed methods and/or block diagrams through the software package.

Figure 5A:
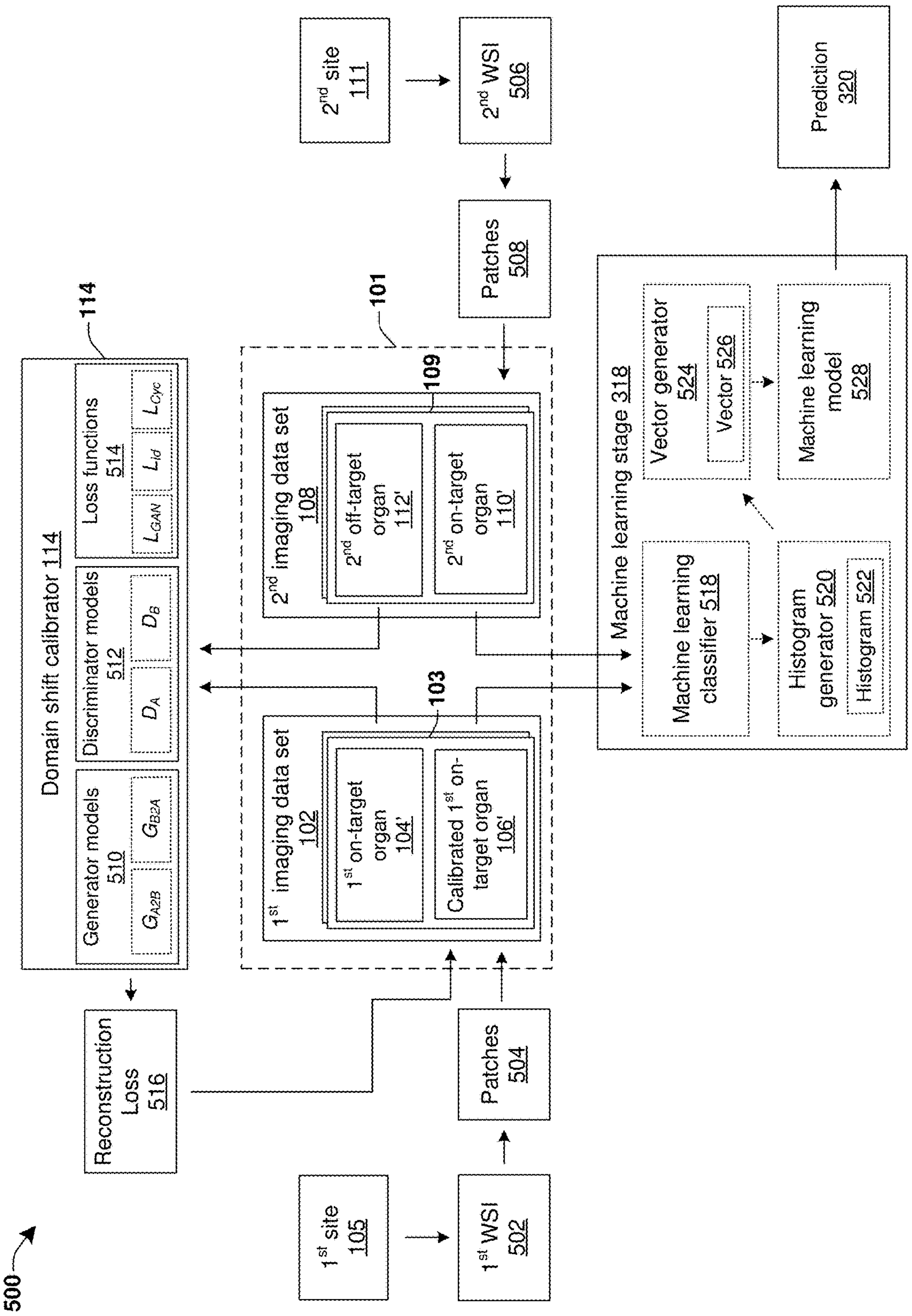
FIG. 5A illustrates a block diagram corresponding to some additional embodiments of a disclosed multi-site cross-organ calibrated machine learning system comprising a domain shift mitigation apparatus.

FIG. 5A illustrates a block diagram corresponding to some additional embodiments of a disclosed multi-site cross-organ calibrated machine learning system 500 comprising a disclosed domain shift mitigation apparatus.

The multi-site cross-organ calibrated machine learning system 500 comprises a memory 101 configured to store a first imaging data set 102 comprising one or more first images 103 from a first site 105 and a second imaging data set 108 comprising one or more second images 109 from a second site 111. The one or more first images 103 respectively comprise a first on-target organ 104'. The one or more second images 109 respectively comprise a second on-target organ 110' and a second off-target organ 112'. In some embodiments, a first WSI 502 may be generated at the first site 105 and a second WSI 506 may be generated at the second site 111. The first WSI 502 may be broken into a first plurality of patches 504 that cover the first WSI 502. The first plurality of patches 504 may be subsequently stored in the first imaging data set 102 as the one or more first images 103 (e.g., as first on-target patches). The second WSI 506 may be broken into a second plurality of patches 508 that cover the second WSI 506. The second plurality of patches 508 may be stored in the second imaging data set 108 as the one or more second images 109 (e.g., as second on-target patches and second off-target patches). In some embodiments, the memory 101 may also store additional images (e.g., corresponding to one or more additional images 322 of FIG. 3) and a calibrated additional on-target organ as described in FIG. 3.

Figure 5B:
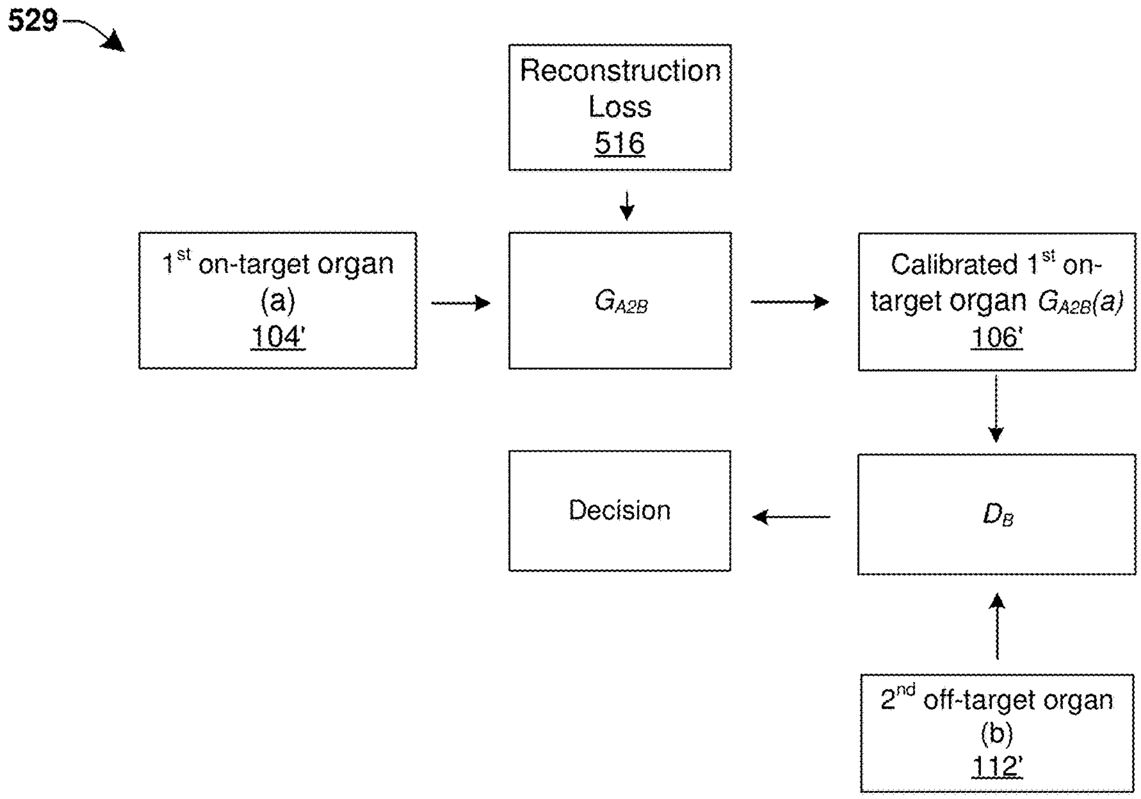
FIG. 5B illustrates some embodiments of block diagrams corresponding to domain mapping paths between images of a disclosed domain shift mitigation apparatus.
Figure 5B:
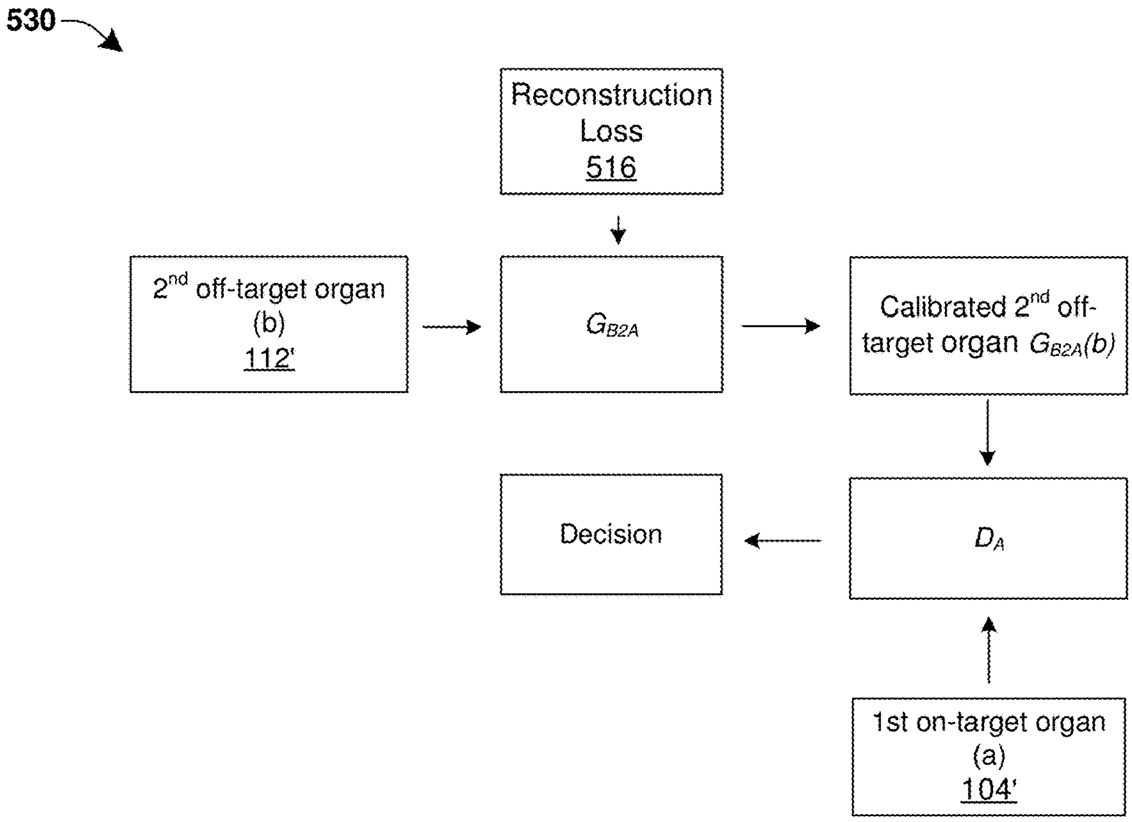

A domain shift calibrator 114 is configured to access the first imaging data set 102 and the second imaging data set 108. The domain shift calibrator 114 is configured to generate mappings between a first domain (A) of the first imaging data set 102 and a second domain (B) of the second imaging data set 108 (e.g., A→B and B→A). In some embodiments, the domain shift calibrator 114 comprises a Cycle Generative Adversarial Network (CycleGAN) based calibration framework configured to represent mappings between the domains along two paths: A→B and B→A using one or more generator models 510 and one or more discriminator models 512. FIG. 5B illustrates some embodiments of a block diagram 529 corresponding to path A→ and a block diagram 530 corresponding to path B→A. In some embodiments, the disclosed domain shift calibrator 114 may be trained until images output of the CycleGAN converge with images of the first imaging data set (e.g., along path A→B) images of the second imaging data set (e.g., along path B→A).

As shown in FIGS. 5A and 5B, path A→B includes a first generator model ($G_{A2B}$) which accepts images produced from the first site 105 and attempts to modify them such that they appear like images produced at the second site 111. Path A→B also includes a first discriminator model ($D_B$) that attempts to determine if the images generated by the first generator model ($_{A2B}$) are distinguishable from the images from the second site 111. Path B→A includes a second generator model ($G_{B2A}$) which accepts images produced from the second site 111 and attempts to modify them such that they appear like images produced at the first site 105. Path B→A also includes a second discriminator model ($D_A$) that attempts to determine if the images generated by the second generator model ($G_{B2A}$) are distinguishable from the images from the first site 105. By using two paths, the domain shift calibrator 114 is able to achieve more robust results compared to a single path.

In some embodiments, the domain shift calibrator 114 is configured to utilize one or more loss functions 514 to determine a difference between the first on-target organ 104' and the second off-target organ 112'. In some embodiments, the one or more loss functions 514 may comprise a minimax GAN loss ($L_{GAN}$), an identity loss Lld, and/or a cycle consistency loss ($L_{Cyc}$), as provided below:

$$L_{GAN}(G_{A2}, D_B, a, b) = \mathbb{E}[\log D_B(b)] + \mathbb{E}[1 - \log D_B(G_{A2B}(a))];$$

$$L_{Id}(G_{A2}, G_{B2A}) = \mathbb{E}[\|G_{A2B}(b) - b\|1] + \mathbb{E}[\|G_{B2A}(a) - a\|1];$$

-continued and $$L_{Cyc}(G_{A2}, G_{B2A}) = \mathbb{E}[\|G_{B2A}(GA2B(a)) - a\|1] + \mathbb{E}[\|GA2B(GB2A(b)) - b\|1].$$

The notation $\mathbb{E}$ represents an expectation value. $L_{GAN}$ represents adversarial component balancing between the first discriminator model ($D_B$) and the first generator model ($GA_{2B}$). It measures an ability of the first discriminator model ($D_B$) to recognize whether an image is actually from the second site 111 or has been generated by the first generator model ($G_{A2B}$). This loss is minimized when a Jensen-Shannon distance between data from the first site 105 matches data from the second site 111, after being modified by the first generator model ($G_{A2B}$). Intuitively, this implies that for images from the first site 105, the associated images generated by the first generator model ($G_{A2B}$) are similar to images from second site 111, suggesting that the calibration performed by domain shift calibrator 114 was successful. Terms $L_{Cyc}$ and $L_{Id}$ serve as regulators encouraging the first generator model ($G_{A2B}$) to learn a model which produces images similar to those in second site 111.

It has been appreciated that GANs may affect the fidelity of tissue attributes in terms of morphology and cytology. For instance, GANs may introduce artifacts due to the loss of high-frequency content, and are also capable of learning histologic features other than pre-analytic variations (e.g., stain) from a template. To mitigate such effects, a reconstruction loss 516 may added between the calibration input and outputs for both paths: a and $G_{A2}$(a), as well b and $G_{B2A}$(b), ∀a∈A; ∀b∈B. The reconstruction loss 516 ($\tilde{L}$) may be as follows:

$$\tilde{L} = \frac{\mathbb{E}[\|G_{A2B}(a) - a\|_1]}{H_a \times W_a \times C_a},$$

where Ha, Wa, and Ca denote a height, width, and channel depth of an arbitrary input image a, respectively. The reconstruction loss 516 quantitatively measures and monitors pixel-wise changes between a and $G_{A2B}$(a), during and after training, to help preserve the stylistic and spatial attributes in the tissue of images within the first imaging data set 102 after calibration. In some embodiments, pixel values during the computation of the reconstruction loss 516 are normalized to be within the range [0,1].

In some embodiments, after calibration, a plurality of patches corresponding to the calibrated first on-target organ 106' are provided to a machine learning stage 318 that is configured to generate a medical prediction 320 corresponding to a patient. In some embodiments, the machine learning stage 318 may comprise a first machine learning classifier 518 that is configured to identify respective patches as having a subtype of tumor (e.g., BCC, SCC-In Situ, SCC-Invasive) or being benign. In some embodiments, the respective patches may be assigned a patch level class prediction score based upon the first machine learning classifier 518. A histogram generator 520 is configured to utilize the subtype of the first plurality of patches 504 to form a patient-level subtype histogram 522. A vector generator 524 is configured to utilize the patient-level subtype histogram 522 to form a vector 526 that is subsequently provided to a machine learning model 528. Based upon the vector 526, the machine learning model 528 is configured to generate a medical prediction 320 (e.g., classify a type and/or sub-type of cancer) for a patient. In other embodiments, the machine learning stage 318 may exclude the histogram generator 520 and the vector generator 524, so that an output of the first machine learning classifier 518 is concatenated and used by machine learning model 528 to generate the medical prediction 320. In yet other embodiments, the machine learning stage 318 may comprise a machine learning model (e.g., a multi-instance machine learning model) that is configured to generate the medical prediction 320 using the calibrated first on-target organ 106' as an input.

Figure 6:
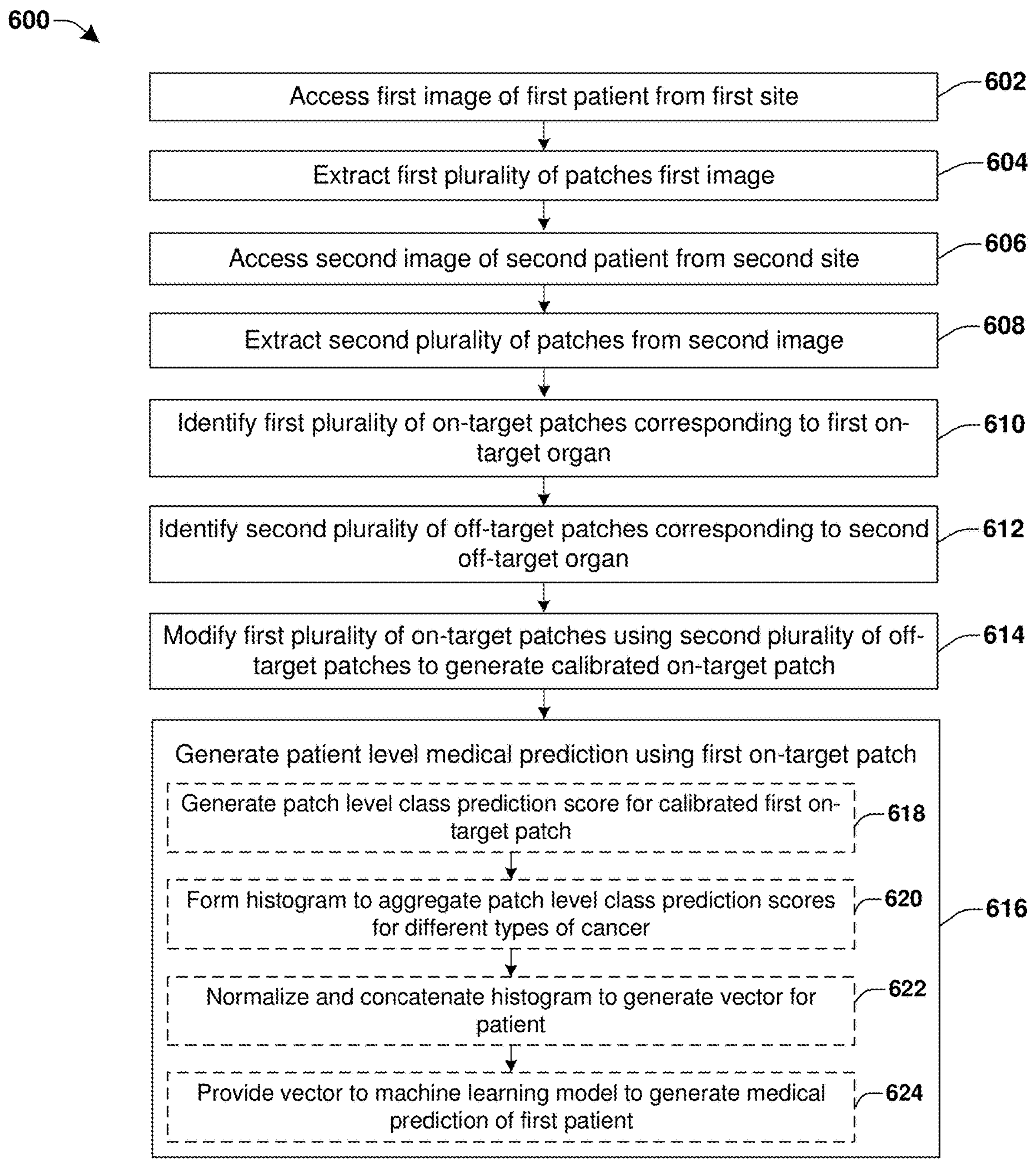
FIG. 6 illustrates a flow diagram of some additional embodiments of a method of mitigating domain shift in an imaging data set.

FIG. 6 illustrates a flow diagram of some embodiments of a method 600 of mitigating domain shift effects in an imaging data set.

At act 602, a first image of a first patient from a first site is accessed.

At act 604, a first plurality of patches are extracted from the first image.

At act 606, a second image of a second patient from a second site is accessed.

At act 608, a second plurality of patches are extracted from the second image.

At act 610, a first plurality of on-target patches corresponding to a first on-target organ are identified.

At act 612, a second plurality of off-target patches corresponding to a second off-target organ are identified.

At act 614, the first plurality of on-target patches are modified using the second plurality of off-target patches to generate a plurality of calibrated first on-target patches.

At act 616, a patient level medical prediction is generated from the first on-target patch. In some embodiments, the patient level medical prediction may be generated according to acts 618-624. In other embodiments (not shown), the patient level medical prediction may be generated by applying an end-to-end machine learning model to the first on-target patch.

At act 618, a patch level class prediction score is generated for a calibrated first on-target patch.

At act 620, the patch level class prediction score is used to form a histogram for different types of cancer. In some embodiments, acts 616-620 may be iteratively performed to form the histogram by aggregating the patch level class prediction scores from the plurality of first on-target patches. In some embodiments, new testing patient data may be generated by request and provided to the machine learning model and used within one or more iterations of the method to generate a patch level class prediction score.

At act 622, the histogram is normalized and concatenated to generate a vector for a patient.

At act 624, the vector is provided to a machine learning model to generate a medical prediction of the first patient.

Figure 7:
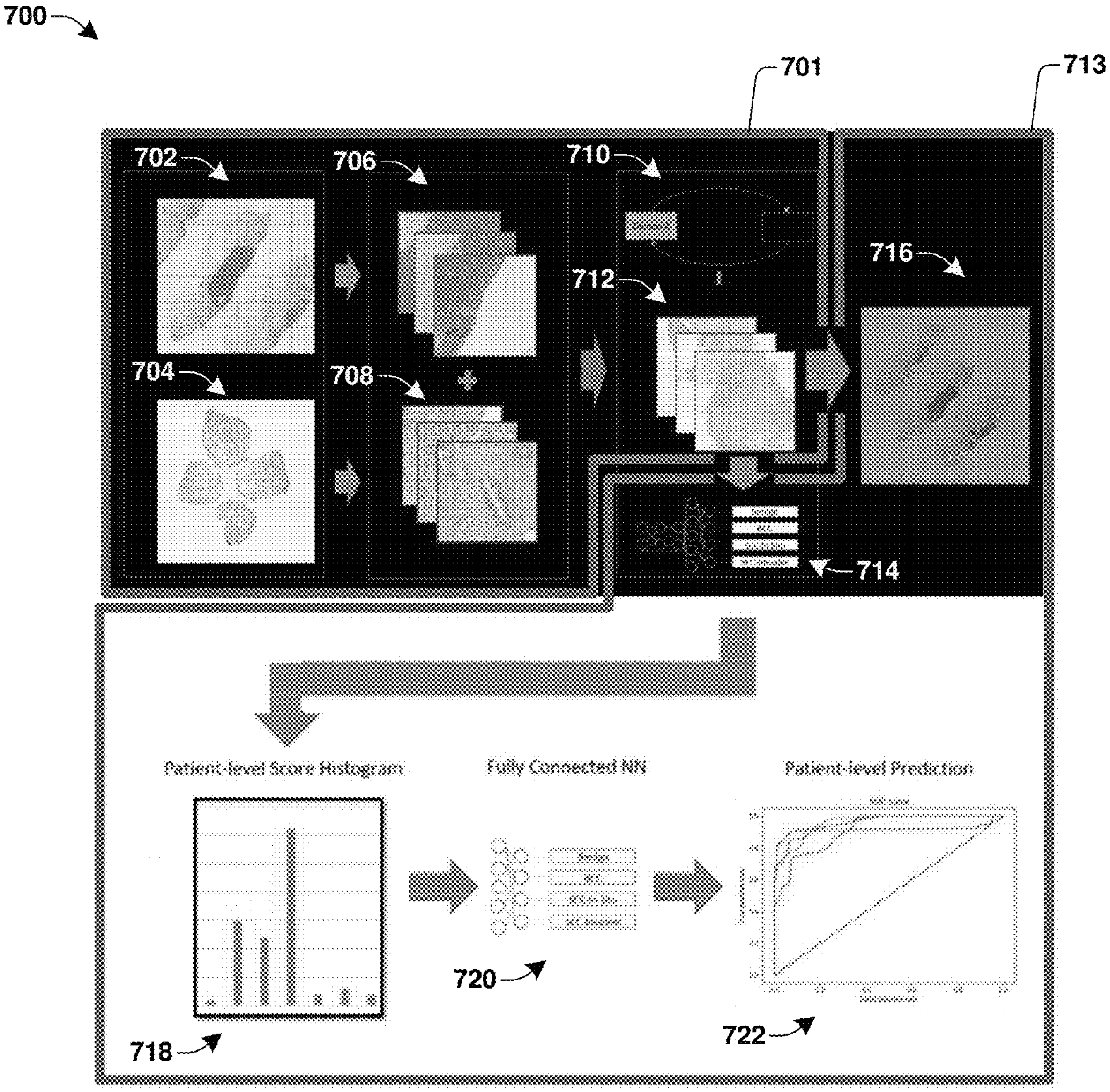
FIG. 7 illustrates a process flow corresponding to a method (e.g., as shown in FIG. 6) of mitigating domain shift in an imaging data set.

FIG. 7 illustrates a process flow 700 corresponding to a method of mitigating domain shift effects in an imaging data set (e.g., as shown in FIG. 6).

As shown in process flow 700, within a calibration stage 701 a first WSI 702 comprising a first on-target organ and a second WSI 704 comprising a second off-target organ are provided. A first plurality of on-target patches 706 are extracted from the first WSI 702 and a second plurality of off-target patches 708 are extracted from the second WSI 704. The first plurality of on-target patches 706 correspond to the first on-target organ and the second plurality of off-target patches 708 correspond to the second off-target organ. The first plurality of on-target patches 706 and the second plurality of off-target patches 708 are provided to a domain shift calibrator 710. The domain shift calibrator 710 is configured to use one or more of the second plurality of off-target patches 708 to calibrate the first plurality of on-target patches 706 and generate a plurality of calibrated of on-target patches 712.

The plurality of calibrated of on-target patches 712 may be subsequently operated upon by a down-stream machine learning stage 713. In some embodiments, the machine learning stage 713 may comprise a first machine learning model 714 configured to classify the plurality of calibrated of on-target patches 712. In some embodiments, a plurality of WSI level saliency maps 716 may be generated from the plurality of calibrated of on-target patches 712. The plurality of WSI level saliency maps 716 can be used to identify a location of cancer within images. In some embodiments, a class prediction score, which identifies a patch as being benign or having a type of cancer, is generated from the plurality of calibrated of on-target patches 712. In some embodiments, the class prediction score is used to generate a patient-level histogram 718, which is subsequently provided to a machine learning model 720 that is configured to generate a patient level prediction 722 (e.g., a prediction of tissue within the first WSI as being benign or being a certain type of cancer). In other embodiments, the machine learning stage 713 may comprise a different configuration. For example, the machine learning stage 713 may comprise a model (e.g., multi-instance learning based model) that is configured to single patient-level prediction from multiple patches without incurring any intermediate results such as patch-level scores.

Figure 8:
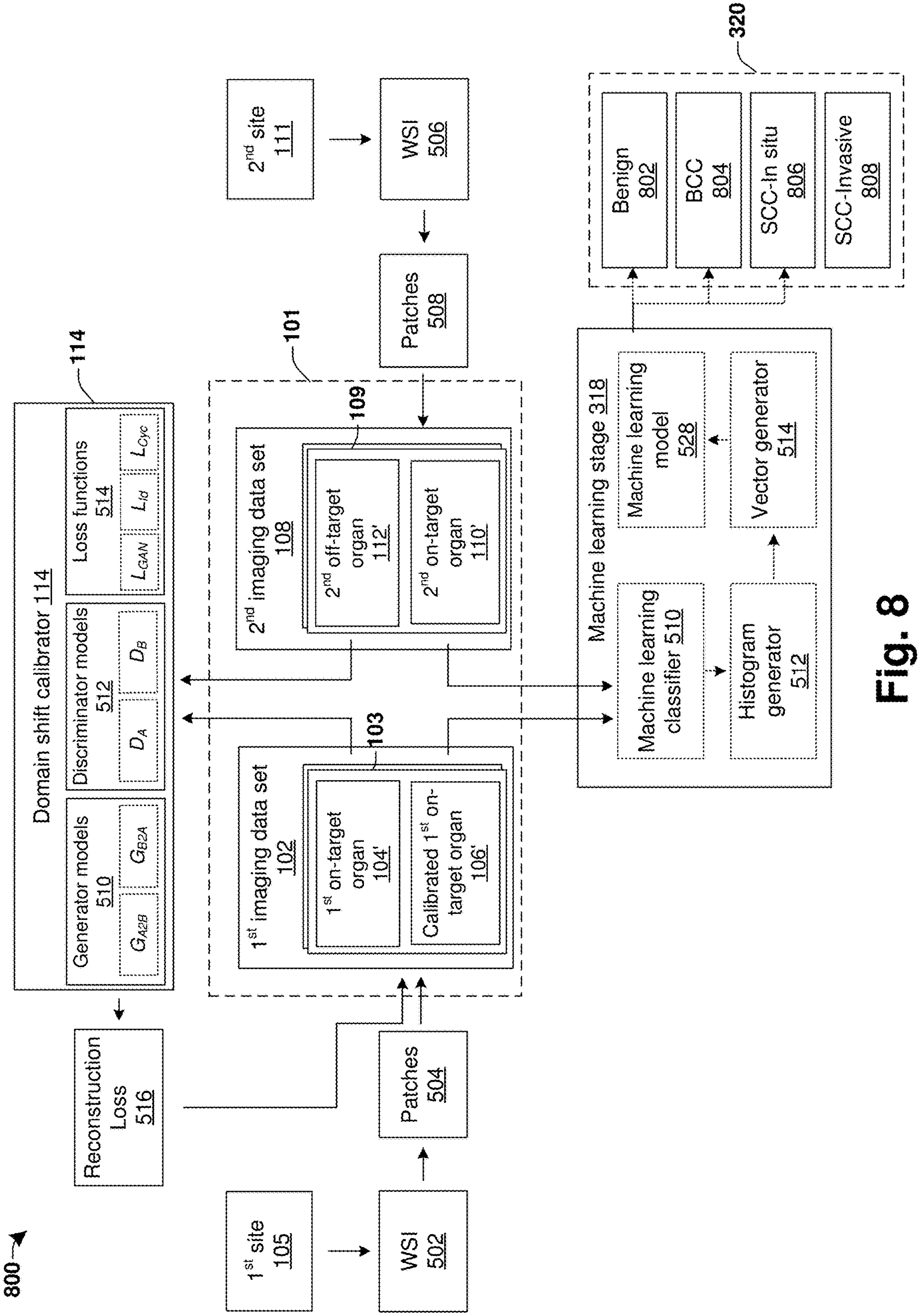
FIG. 8 illustrates a block diagram corresponding to some embodiments of a multi-site cross-organ calibrated machine learning system configured to diagnose non-melanoma skin cancer (NMSC).

FIG. 8 illustrates a block diagram corresponding to some embodiments of a multi-site cross-organ calibrated machine learning system configured to diagnose non-melanoma skin cancer (NMSC). While FIG. 8 illustrates a block diagram that applies the disclosed multi-site cross-organ calibrated machine learning system to a specific application of diagnosing NMCS, it will be appreciated that the disclosed multi-site cross-organ calibrated machine learning system is not limited to such applications.

The multi-site cross-organ calibrated machine learning system 800 comprises a memory 101 configured to store a first imaging data set 102 that includes one or more first images 103 from a first site 105 and a second imaging data set 108 that includes one or more second images 109 from a second site 111. In some embodiments, the one or more first images 103 may comprise training data and the one or more second images 109 may comprise testing data. In such embodiments, the one or more first images 103 respectively include a first on-target organ 104' that is and/or comprises cells from skin tissue. The one or more second images 109 respectively comprise a second on-target organ 110' and a second off-target organ 112'. In some embodiments, the second on-target organ 110' may comprise or be cells from skin tissue and the second off-target organ 112' may comprise or be cells from lung tissue.

A domain shift calibrator 114 is configured to access a first plurality of patches 504 corresponding to the first on-target organ 104' and a second plurality of patches 508 corresponding to the second off-target organ 112'. The domain shift calibrator 114 is configured to use the second plurality of patches 508 to generate a calibrated first on-target organ 106' that mitigates a difference in domain shift between the first on-target organ 104' and the second on-target organ 110'. In some embodiments, the second off-target organ 112' may be selected to resemble the first on-target organ 104' in terms of tissue type (e.g., epithelial or not), stain, and/or composition of tissue histologic structures (e.g., whether keratinization takes place). By selecting off-target template organs to resemble on-target organs, better calibration may be achieved.

After calibration of the first plurality of patches 504, the calibrated first on-target organ 106' is provided to a machine learning stage 318. In some embodiments, the machine learning stage may be configured to classify the first on-target organ 104' as benign 802, basal cell carcinoma (BCC) 804, in-situ squamous cell carcinoma (SCC-In situ) 806, or invasive squamous cell carcinomas (SCC-Invasive) 808. Typically, a domain shift degrades deep learning classification performance to an extent that makes it extremely difficult to distinguish the subtypes of SCC (e.g., SCC-In Situ versus SCC-Invasive). However, the reduction of domain shift achieved by the domain shift calibrator 114 improves an accuracy of the machine learning stage 318 and makes it possible to distinguish between BCC and SCC and to also distinguish between SCC subtypes (e.g., SCC-in Situ and SCC-Invasive), thereby meaningfully aiding in providing improved diagnosis, prognosis, and treatment management of patients with NMSC.

In some embodiments, the machine learning stage 318 may comprise a first machine learning classifier 518 that is configured to identify respective patches as having a subtype of tumor (e.g., BCC, SCC-In Situ, SCC-Invasive) or benign. A histogram generator 520 is configured to utilize the subtype of the first plurality of patches 504 to form a patient-level subtype histogram 522. A vector generator 524 is configured to utilize the patient-level subtype histogram 522 to form a vector 526 that is subsequently provided to a machine learning model 528.

FIG. 9A illustrates a table 900 showing example comparisons between RGB values of different uncalibrated images.

Table 900 shows a first comparison illustrating p-values (e.g., obtained using a Wilcoxon Rank-sum test of color distribution in terms of brightness) and intensity values between skin tissue within a first imaging data set from a first site ($A_S$) and skin tissue within a second imaging data set from a second site ($B_S$). A second comparison shows p-values and intensity values between skin tissue within the second imaging data set from the second site ($B_S$) and lung tissue within the second imaging data set from the second site ($B_L$) The first and second comparisons show an intensity of red values that are similar, but that the intensity of green values 902 and blue values 904 images are significantly closer between different types of organs from a same site than between a same type of organ from different sites. This indicates that the use of lung tissue from a second site can be used to accurately calibrate skin tissue images from a first site.

FIG. 9B illustrates a table 906 showing example comparisons between RGB values of calibrated and uncalibrated images for different cancer classifications.

Table 906 shows RGB intensity values for a first set of images 908 including uncalibrated skin tissue images from a first site, for a second set of images 910 including images of skin tissue from the first site that have been calibrated using images of lung tissue from a second site, for a third set of images 912 including uncalibrated images of skin tissue from the second site, and a fourth set of images 914 including images of skin tissue from the first site that have been calibrated using images of skin tissue from the second site.

As can be seen from table 906, the calibration of skin tissue from a first site using lung tissue from a second site (e.g., the second set of images 910) causes the RGB intensity of the calibrated images to closely resemble the RGB intensity of images from the second site (e.g., the third set of images 912), thereby showing that the calibration is able to accurately mitigate domain shift between the different data sets. Furthermore, in BCC, SCC-In Situ, and SCC-Invasive, calibration of skin tissue within the first data set using lung tissue from the second site (e.g., the second set of images 910) is able to achieve a closer match with the images from the second site (e.g., the third set of images 912) than calibration of skin tissue within the first data set using skin tissue (e.g., the fourth set of images 914).

Figure 10:
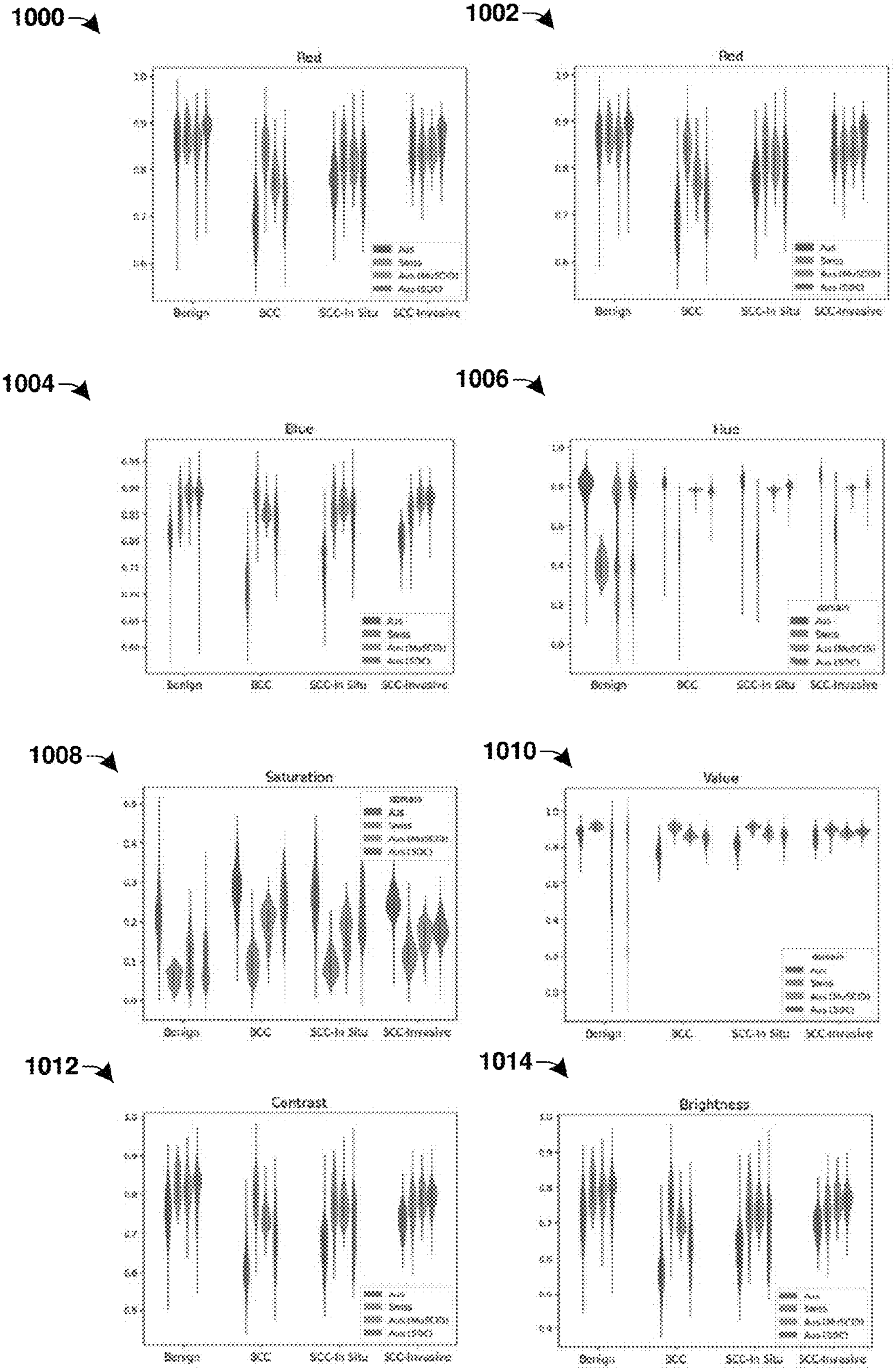
FIG. 10 illustrates exemplary violin plots showing a distribution of RGB intensity, contrast, brightness, and HSV (Sue/Saturation/Value) values of different classes of NMSC with different data sets.

FIG. 10 illustrates exemplary violin plots 1000-1014 showing a distribution of RGB intensity, contrast, brightness, and HSV values of different classes of cancer with different data sets.

The exemplary violin plots 1000-1014 show a distribution of RGB intensity 1000-1004, a distribution of HSV (Hue/Saturation/value) 1006-1010, a distribution of contrast 1012, and a distribution of brightness 1014 for different classes of cancer (shown on x-axis) including benign, BCC, SCC-In Situ and SCC-Invasive. The distributions are shown for a first data set from a first site (e.g., AUS), a second data set from a second site (e.g., Swiss), a third data set from the first site that has been calibrated with off-target images from a second site using the disclosed apparatus (e.g., Aus (MuSCID)), and a fourth data set from the first site that has been calibrated with a same organ from the second site (e.g., Aus (SOC)).

The violin plots 1000-1014 show that calibration with off-target organs from a second site using the disclosed apparatus mitigates differences in contrast and color distribution. For example, in violin plot 1000 the first data set has a significantly larger distribution of red color values than the second data set indicating variance in visual characteristics between the data sets. Furthermore, the high probability of red color values is offset from that of the second data set further indicating a variance in visual characteristics. The third data set (calibrated data set) has a smaller distribution of red color values and a larger overlap with the second data set indicating less variance in visual characteristics.

Figure 11:
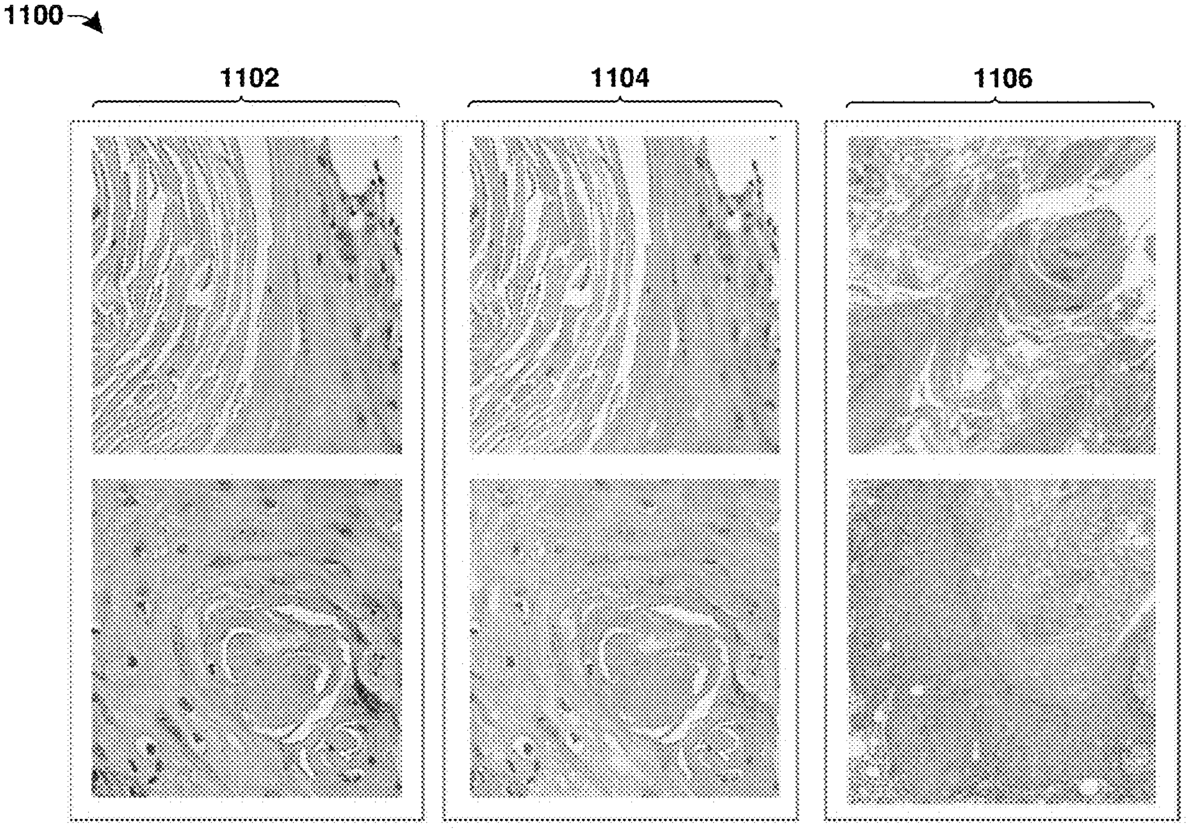
FIG. 11 shows exemplary images showing keratin and/or a region with keratinization within different data sets of tissue from SCC-Invasive lesions.

FIG. 11 shows exemplary images 1100 showing keratin and/or a region with keratinization within different data sets of tissue from SCC-Invasive lesions.

The exemplary images 1100 of FIG. 11 comprise a first pair of images of skin tissue 1102 from a first data set, a second pair of images of skin tissue 1104 from a second data set, and a third pair of images of skin tissue 1106 from a third data set. The first data set is from a first site and the first pair of images of skin tissue 1102 have not been calibrated. The second data set is from a second site and the second pair of images of skin tissue 1104 have been calibrated based on an off-target lung tissue. The third data set is from a third site and the third pair of images of skin tissue 1106 have not been calibrated.

It has been appreciated that keratinization and keratin pearls are commonly observed in well differentiated SCC-Invasive. Keratinization and keratin pearls in both the first pair of images of skin tissue 1102 and the third pair of images of skin tissue 1106 have a pink/red appearance. However, keratin only exists in lung tissue under abnormal circumstances (e.g., lung squamous cell carcinoma). Due to the general absence of keratin in lung tissue templates, the calibration of keratin regions in the first data set is likely affected, resulting in the keratin in the second pair of images of skin tissue 1104 appearing bluer than the keratin in third pair of images of skin tissue 1106, and thus potentially impacting the blue channel metrics. This supports the selection of off-target organs that resemble the on-target organ, in terms of tissue type (e.g., epithelial or not), stain, and composition of tissue histologic structures (e.g., whether keratinization takes place).

Figure 12:
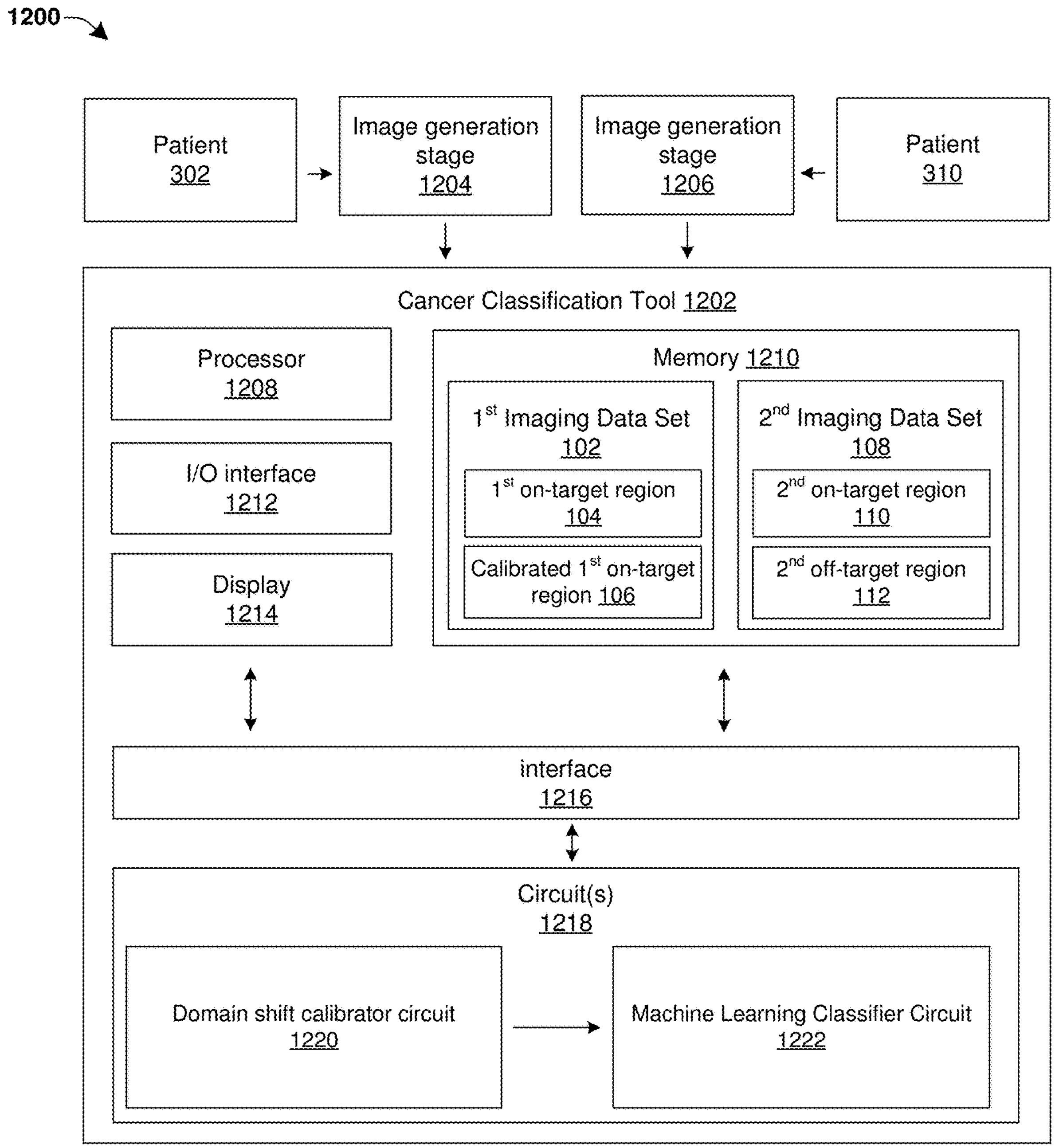
FIG. 12 illustrates a block diagram of some embodiments of a prognostic apparatus comprising a disclosed machine learning system comprising a domain shift mitigation apparatus.

FIG. 12 illustrates a block diagram of some embodiments of a prognostic apparatus 1200 comprising a disclosed domain shift calibrator.

The prognostic apparatus 1200 comprises a cancer classification tool 1202. The cancer classification tool 1202 is configured to receive imaging data from a plurality of image generation stages 1204-1206 at different sites (e.g., different hospitals, universities, and/or the like).

The cancer classification tool 1202 comprises a processor 1208 and a memory 1210. The processor 1208 can, in various embodiments, comprise circuitry such as, but not limited to, one or more single-core or multi-core processors. The processor 1208 can include any combination of general-purpose processors and dedicated processors (e.g., graphics processors, application processors, etc.). The processor 1208 can be coupled with and/or can comprise memory (e.g., memory 1210) or storage and can be configured to execute instructions stored in the memory 1210 or storage to enable various apparatus, applications, or operating systems to perform operations and/or methods discussed herein.

Memory 1210 can be further configured to store a first imaging data set 102 comprising the one or more first images (e.g., digitized WSIs) from a first site and a second imaging data set 108 comprising the one or more second images (e.g., digitized WSIs) from a second site. The one or more images from the first site include a first on-target region 104 (e.g., organ). The one or more images from the second site include a second on-target region 110 (e.g., organ) and a second off-target region 112 (e.g., organ). The one or more images respectively include a plurality of imaging units (e.g., pixels, voxels, etc.) respectively having an associated intensity pixels. In some embodiments, the first imaging data set 102 may be stored in the memory 1210 as a training set and the second imaging data set 108 may be stored in the memory 1210 as a testing set for training a machine learning circuit.

The cancer classification tool 1202 further comprises an input/output (I/O) interface 1212 (e.g., associated with one or more I/O devices), a display 1214, one or more circuits 1218, and an interface 1216 that connects the processor 1208, the memory 1210, the I/O interface 1212, the display 1214, and the one or more circuits 1218. The I/O interface 1212 can be configured to transfer data between the memory 1210, the processor 1208, the one or more circuits 1218, and external devices (e.g., image generation stages 1204-1206).

In some embodiments, the one or more circuits 1218 may comprise hardware components. In other embodiments, the one or more circuits 1218 may comprise software components. In such embodiments, the one or more circuits 1218 may execute code stored in the memory 1210. The one or more circuits 1218 can comprise a domain shift calibrator circuit 1220 configured to modify the first on-target region 104 based on the second off-target region 112 to generate a calibrated first on-target region 106.

In some additional embodiments, the one or more circuits 1218 may further comprise a machine learning classifier circuit 1222. In some embodiments, the machine learning classifier circuit 1222 is configured to operate upon the calibrated first on-target region 106 to generate a medical prediction of a patient. In some alternative embodiments, the machine learning classifier circuit 1222 is configured to operate upon the calibrated first on-target region 106 and/or the second on-target region 110 to generate a model that accurately classifies cancer.

Example Use Case

We evaluated a multi-site cross-organ calibrated deep learning (MuSCID) model for identifying and distinguishing: (a) basal cell carcinoma (BCC), (b) in-situ squamous cell carcinomas (SCC-In Situ), and (c) invasive squamous cell carcinomas (SCC-Invasive), using an Australian (training, n=85) and a Swiss (held-out testing, n=352) cohort. Our experiments reveal that MuSCID model reduces the Wasserstein distances between sites in terms of color, contrast, and brightness metrics, without imparting noticeable artifacts to training data. The NMSC-subtyping performance is statistically improved as a result of MuSCID model in terms of one-vs. rest AUC: BCC (0.92 vs 0.87, p=0.01), SCC-In Situ (0.87 vs 0.73, p=0.15) and SCC-Invasive (0.92 vs 0.82, p=1e-5). Compared to baseline NMSC-subtyping with no calibration, the internal validation results of MuSCID (BCC (0.98), SCC-In Situ (0.92), and SCC-Invasive (0.97)) suggest that while domain shift indeed degrades classification performance, our on-target calibration using off-target tissue can safely compensate for pre-analytical variabilities, while improving the robustness of the model.

It has been appreciated that site-specific pre-analytic variables imparted into WSI are sufficiently similar between organs, such that images from a second "off-target" organ (i.e., an organ not employed in the training and testing of a corresponding diagnosis task) can be used as a template for calibration of the primary on-target organ, thus yielding performance improvements for the target task. The usage of off-target organs for on-target calibration is thus termed "cross-organ" calibration. To validate the disclosure, we measured improvement in the performance of a DL-based non-melanoma skin cancer (NMSC) subtyping classifier after calibrating the skin training images with lung template images, an approach we term Multi-site Cross-organ Calibration Deep Learning (MuSCID). Our subtyping classifier is trained using an Australian cohort (n=85) to distinguish between different subtypes of non-melanoma skin cancer: benign, basal cell carcinoma (BCC), in-situ squamous cell carcinoma (SCC), and invasive SCC. This NMSC-subtyping model is subsequently evaluated on an independent Swiss cohort (n=352). Lung tissue samples from the Swiss site were employed as templates for MuSCID of the Australian data, in order to help mitigate domain shift effects. This lung tissue naturally shares similar variables associated with laboratory equipment (e.g., microtome, scanner, stainer) and biochemical properties (temperature, humidity, stain), resulting in similar image characteristics to that of skin samples. Additionally, since the lung and skin tissue are unrelated to each other, the use of cross-organ information helps mitigate the possibility of data leakage. We also demonstrate that despite the differences in lung and skin tissue morphology, the fidelity of calibration outputs is retained.

We use A to represent the data of the training site, and B to represent data from the testing site. Unless otherwise specified, we use a to represent individual images of site A, and b to represent images of site B. For the notation $\forall a \in A$ and $\forall b \in B$ defined above, we use the subscript T to denote the type of tissue organ that is either skin (S) or lung (L) tissue ($\tau \in \{S,L\}$). For calibration outputs, we use the superscript $\mu$ to denote the type of tissue organ (S or L) that was employed as template ($\mu \in \{S,L\}$). The relevant notation used in this work is illustrated in Table 1 below.

TABLE 1

Notation table for sites and organs

| Notation | Definition |
|---|---|
| A | Training Site |
| B | Testing Site |
| S | Skin Tissue |
| L | Lung Tissue |
| $A_S$ | Skin Slides from site A |
| $A_S^L$ | Skin Slides from site A calibrated with Lung Templates (MuSCID) |
| $A_S^S$ | Skin slides from site A calibrated with Skin Templates (SOC) |
| $B_S$ | Skin Slides from B |
| $B_L$ | Lung Slides from B |
| G | Generator networks in CycleGAN |
| D | Discriminator networks in CycleGAN |
| $M_C$ | Downstream classification model trained with calibrated data |
| $M_N$ | Downstream classification model trained with un-calibrated data |

A summary of the cohorts employed in this study is illustrated in Table 2. The datasets comprised H&E WSI collections obtained from two international sites: (a) Cohort from site A (n=85) patients used for training from Southern Sun Pathology, Australia, and (b) Cohort from site B (n=352) patients from Kantonsspital Aarau, Switzerland used for testing. To model the pre-analytic properties anticipated in cohort B, four WSIs of lung specimens ($B_L$) were employed from site B to calibrate skin slides from site A ($A_S$). The lung specimens $B_L$ were prepared in a similar manner (e.g., stainer, tissue thickness, and slide scanner) as skin specimens from site B ($B_S$), while coming from patients not part of the NMSC cohort. All data in site B was collected at 40× magnification and down-sampled to 20× in order to approximate the resolution of the images originating from site A.

TABLE 2

Composition of Cohorts. WSIs in A were scanned at a magnification of 20x. WSIs in B were scanned at a 40x magnification and down-samples to 20x during pre-processing to approximate the resolution of slides in A.

| | Training Cohort from site A (Australia) | | | Testing Cohort from site B (Switzerland) | |
|---|---|---|---|---|---|
| | # Patients | # WSI | # Patches | # Patients | # WSI |
| Benign | 11 | 13 | 7905 | 9 | 9 |
| BCC | 54 | 70 | 2652 | 131 | 131 |
| SCC-In Situ | 10 | 12 | 3132 | 12 | 12 |
| SCC-Invasive | 10 | 11 | 2216 | 200 | 200 |
| Total | 85 | 106 | 15905 | 352 | 352 |

A ResNext50_32×4D architecture was selected for the NMSC-subtyping DL classifier. This classifier was chosen given its previously demonstrated high predictive performance with comparatively few parameters compared to other DL architectures. Image patches of size 512×512 were extracted at 20× from regions of tumor annotated by human dermatopathologists in slides from site A. Stain augmentation was employed during training of all DL networks. Patient-level predictions were generated by aggregating patch-level predictions throughout the WSIs. Briefly, each patch was classified by the NMSC subtype classifier into one of four target classes: benign, BCC, SCC-In Situ, and SCC-Invasive. The ResNext50_32×4d classifier outputs the class prediction scores for each image patch. For each of the three cancer classes, a 32-bin histogram is created to aggregate the patch-level raw class output values. Each of the three histograms corresponding to the three cancer classes was then normalized and concatenated, resulting in a 1×96 vector signature for each patient. This vector was employed as the input for training a fully connected neural network for predicting the final patient-level output.

MuSCID was trained until the reconstruction loss $\tilde{L}$ between images from site A (a) and generator model $G_{A2B}$ (a) (a generator model ($G_{A2B}$) which accepts images produced from the site A and attempts to modify them such that they appear like images produced at the site B) converged, and $G_{A2B}$ (a) qualitatively resembled the pre-analytic appearance (e.g., stain) of $B_L$.

Experiment 1: Evaluation of MuSCID in Terms of Consistency of Skin Tissue Components and Color Distribution The main premise behind Experiment 1 is that differences in image presentation between NMSC images from site A and site B can be ameliorated with MuSCID by using $B_L$ images from the Swiss site while not imbuing it with significant histologic variations. A variety of evaluation strategies were employed for Experiment 1 as described below.

Image metrics capturing the (a) brightness, (b) root mean square (RMS) contrast, and (c) mean intensity of each of the red/green/blue (RGB) and hue/saturation/value (HSV) channels are computed from the skin and lung slides of both site A and site B to examine the relative inter-site variability. Swiss lung images, $B_L$, are also analyzed in a similar fashion to determine their suitability for serving as template surrogates for $B_S$. Violin plots were employed to visualize the image metric distributions. Besides the distribution distance, a Wilcoxon rank-sum test was also used to determine if image metric distributions between $A_S$ and $B_S$ are statistically significant.

MuSCID was employed to calibrate Australian NMSC images with $B_L$ (Swiss lung). If MuSCID is successful at compensating for pre-analytical variance between site A and site B, the distance between image metrics from $$A_S^L$$

and $B_S$ should be reduced. To demonstrate this reduction for each subtype, two image metrics for all four subtypes (benign/BCC/SCC-In Situ/SCC-Invasive) are computed between $$A_S^L$$

and $B_S$. First, Wassertein distance, a commonly invoked metric for evaluation of domain shift, was employed to compare RGB and contrast values, wherein smaller Wasserstein distances indicate greater similarity. Additionally, a Wilcoxon rank-sum test was used to determine if the image metrics of $$A_S^L$$

are statistically different from $A_S$. A reduction in Wasserstein distance between $$A_S^L$$

and $B_S$ would suggest that calibration was performed successfully and the previously identified domain shift had been ameliorated. It should be noted that, since Wilcoxon rank-sum test also considered other factors of distributions (e.g., distribution shape) than their distances, a statistically significant p-value between $$A_S^L$$

and $B_S$ does not suggest that the calibration is unsuccessful.

To evaluate the benefit of including the reconstruction loss $\tilde{L}$ in MuSCID, we both qualitatively and quantitatively compared reconstruction loss $\tilde{L}$ in the inference stage with and without optimizing reconstruction loss $\tilde{L}$ during the training stage. We hypothesized that the inclusion of reconstruction loss $\tilde{L}$ during the model optimization process would encourage the retention of consistency in the histologic appearance of the skin while limiting the introduction of lung morphology during the calibration of $A_S$ to $$A_S^L.$$

To visually and qualitatively assess the impact of calibration on $$A_S^L,$$

512 4096×4096 regions of interest (ROIs) were inspected by a dermatopathologist. These 512 ROIs consisted of: 51 benign, 336 BCC, 70 SCC-In Situ, and 55 SCC-Invasive cases. During the inspection, the dermatopathologist was informed of the disease type of the ROIs, and requested to report any observed skin histology alterations or calibration artifacts.

For further comparison, skin templates $B_S$ were employed for calibration to produce $$A_S^S.$$

Discrepancies between $$A_S^L \text{ and } A_S^S$$

were visually evaluated in terms of tissue texture and color space qualities to better understand the potential consequences of data leakage.

To the best of our best knowledge, a direct method to quantitatively assess data leakage during calibration does not exist. As a surrogate measure, Haralick texture features and mean nuclei area between $$A_S^L \text{ and } A_S^S$$

are compared. This allows us to estimate whether calibration introduces different morphological information into $A_S$ based on the template organ of choice. The publicly available HoverNet model was used to perform nuclei segmentation. This model was selected as it was trained on over 200 k nuclei from multiple data sources, and showed consistently robust model performance during validation. Here we leverage that generalizable performance across our datasets $$(A_S, A_S^L, A_S^S, B_S, \text{ and } B_L)$$

to ensure that nuclei-level features were mostly captured in comparable nuclear regions.

Thirteen nuclear-specific Haralick texture features were extracted within the segmented nuclei regions, along with the mean nuclei area. The Wasserstein distance between each of the feature distributions was computed. Additionally, to measure whether these morphological features are significantly different from each other, the Wilcoxon Rank-sum p-value of these feature distributions between datasets $$(A_S, A_S^L, A_S^S, B_S, \text{ and } B_L)$$

was computed, with a p-value of 0.05 set to determine statistical significance.

Experiment 2: Comparative Evaluation of MC and MN in Terms of AUC for NMSC Diagnosis and Classification We evaluate the NMSC-subtyping models trained with $A_S$ and $$A_S^L,$$

respectively on held-out $D_V$ sampled from $B_S$ and compare their subtyping performance in terms of the area under the curve (AUC) of the corresponding receiver operating characteristic (ROC) curves produced by thresholding the output prediction score of NMSC-subtyping models. The one—vs. rest multi-class AUC is employed as the metric for the prediction. During the held-out testing phase, all patches from the tissue region without artifacts (blurry, pen-marker) are fed into the NMSC-subtyping model. Quality control of patches was assessed using HistoQC, a WSI quality control tool (e.g., blurry and tissue folding identification), along with the manual inspection. The Delong test was used to assess whether the improvement between ROC curves is statistically significant. An additional set of sub-experiments, examining combinations of $D_T$ and internal $D_V$ composed of $A_S$ and $$A_S^L$$

were investigated (see Table 3).

TABLE 3

Description of comparison strategies.

| Comparison Strategy | $D_T$ | $D_V$ | Network Model Used |
|---|---|---|---|
| $E_{A_S,A_S}$ | $A_S$ | $A_S$ | Train from scratch |
| $E_{A_S^L,A_S^L}$ | $A_S^L$ | $A_S^L$ | Train from scratch |
| $E_{A_S,A_S^L}$ | $A_S$ | $A_S^L$ | Reuse $E_{A_S,A_S}$ |
| $E_{A_S^L,A_S}$ | $A^L$ | A | Reuse $E_{A_S^L,A_S^L}$ |
| $E_{A_S^S,A_S^S}$ | $A^S$ | $A^S$ | Train from scratch |
| $E_{A_S^L,B_S}$ | $A_S^L$ | $B_S$ | Reuse $E_{A_S^L,A_S^L}$ |
| $E_{A_S^S,B_S}$ | $A_S^S$ | $B_S$ | Reuse $E_{A_S^S,A_S^S}$ |
| $E_{A_S,B_S}$ | $A_S$ | $B_S$ | Reuse $E_{A_S,A_S}$ |

The letter E represents an experiment with the first subscript indicating the $D_T$ and the second describing the corresponding $D_V$. $A_S$, $A_S^L$, $A_S^S$, and $B_S$ denote the original Australian skin data, the calibrated Australian skin (by Swiss lung), calibrated Australian skin (by Swiss skin), and the held-out $D_V$ of Swiss skin, respectively.

Training data $D_T$ from A was randomly split at the patient level into training data $D_T$ and internal testing data $D_V$ using a ratio of 7:3, such that the distribution of each subtype is preserved. In the first four experiments in Table 3, machine learning models (e.g., deep learning models) were trained and validated on the images coming from the same site, site A. The rationale of these experiments is that if $$E_{A_S^L,A_S^L}$$

has similar performance metrics to that of $E_{A_SA_S}$ then any potential image artifacts introduced by the calibration process minimally affected subtype prediction performance. On the other hand, a difference between performances in $$E_{A_S^L,A_S^L} \text{ vs. } E_{A_S^L,A_S^L}$$

and $$E_{A_S^L,A_S^L} \text{ vs. } E_{A_S^L,A_S^L},$$

would suggest that domain shift between $A_s$ and $$A_S^L$$

degrades the ability of models to generalize. The impact of domain shift between site A and site B, as well as the benefit of calibration, is evaluated in the held-out tests $$E_{A_S^L,B_S} \text{ and } E_{A_S,B}.$$

To better understand the impact of potential data leakage, $B_S$ was employed as a template to calibrate $A_S$ to produce $A_S^S$.

An NMSC-subtyping model was subsequently trained with $A_S$. Similar AUC values between cross-site on- and off-target organ tests (i.e., $$E_{A_S^S,B_S} \text{ and } E_{A_S^L,B_S})$$

would suggest that MuSCID effectively mitigates the domain shift in terms of the NMSC-subtyping performance, while also minimizing the risk of data leakage. The difference between the AUC values $$E_{A_S^S,B_S} \text{ and } E_{A_S^L,B_S}$$

was again evaluated by the Delong test.

Deep learning (DL) models are often considered "black-box" since there is a lack of interpretability or understanding of what DL models learn in order to succeed. To obtain a WSI level view of the DL's capability of tumor localization, a heatmap of patch prediction scores is generated and overlaid on the original image. (See, e.g., FIG. 7). Grad-CAM is used to visualize regions in the patches that are most informative to the model when making a prediction. If these highlighted regions contain relevant information for identifying NMSC subtypes, it suggests that our DL model has successfully learned clinically discriminating features. Lastly, 2D t-distributed Stochastic Neighbor Embedding (t-SNE) plots of the high dimensional feature space may be formed by the NMSC-subtyping model. The t-SNE shows whether the clustering of features is stratified by the disease type, and potentially identifies difficult cases falling on the boundary between the subtype clusters.

Experiment 1 Results and Discussion: Evaluation of MuSCID in Terms of Consistency of Skin Tissue Components and Color Distribution The impact of domain shift across the Australian (A) and Swiss (B) sites is evident, observable by the inconsistency between the intensities of the green and blue channels in Table 4. FIG. 2A illustrates the necessity for calibration to mitigate the impact of such domain shift for the multi-site generalizability of NMSC-subtyping between site A and site B. The violin plots in FIG. 2A also show that the intra-site color distribution difference between $B_S$ and $B_L$ is less severe than that of the inter-site color distribution difference between $A_S$ and $B_S$, especially in terms of green and blue channel intensity statistics. There is also a large difference in the saturation channel intensity statistics of the HSV representation between $A_S$ and B. Moreover, the Wilcoxon rank-sum test in Table 5 also illustrates that the domain shift in terms of the difference of color distribution between $A_S$ and $B_S$ is significant (p=3×10−105). Interestingly, Table 5 shows that $B_L$ is much closer to $B_S$ than AS in terms of the green (55% closer) and blue channels (75% closer), suggesting that $B_L$ may be suitable as a calibration template for $B_S$.

TABLE 4

The corresponding mean and standard deviation of image metric reported for the corresponding violin plot. We highlight the entries between Australian ($A_S$) and Swiss ($B_S$) skin to illustrate the difference of the mean intensity values in the green and blue channels.

| | Brightness | Contrast | RGB | | HSV | |
|---|---|---|---|---|---|---|
| $A_S$ | 0.75 ± 0.05 | 0.72 ± 0.07 | R | 0.81 ± 0.07 | H | 0.43 ± 0.03 |
| | | | G | 0.63 ± 0.09 | S | 0.69 ± 0.08 |
| | | | B | 0.78 ± 0.05 | V | 0.78 ± 0.10 |
| $B_S$ | 0.78 ± 0.05 | 0.77 ± 0.05 | R | 0.83 ± 0.04 | H | 0.53 ± 0.13 |
| | | | G | 0.72 ± 0.07 | S | 0.11 ± 0.04 |
| | | | B | 0.86 ± 0.03 | V | 0.90 ± 0.02 |
| $B_L$ | 0.65 ± 0.08 | 0.81 ± 0.40 | R | 0.86 ± 0.04 | H | 0.78 ± 0.03 |
| | | | G | 0.76 ± 0.05 | S | 0.15 ± 0.04 |
| | | | B | 0.88 ± 0.02 | V | 0.89 ± 0.02 |

TABLE 5

The p-value is the result of the Wilcoxon Rank-sum test of color distribution in terms of the brightness between (1) $A_S$ and $B_S$; (2) $B_L$ and $B_S$. We also measure the difference in the mean of Red, Green, and Blue intensity values. We highlight the entries to reflect that $B_L$ and $B_S$ are closer to that of $B_S$ compared to $A_S$ in terms of distance in the distribution of green and blue intensity values.

| | p-value | Red | Green | Blue |
|---|---|---|---|---|
| $A_S$ vs. $B_S$ | $3 \times 10^{-105}$ | 0.02 | 0.09 | 0.08 |
| $B_L$ vs. $B_S$ | $8 \times 10^{-218}$ | 0.03 | 0.04 | 0.02 |

Figure 15:
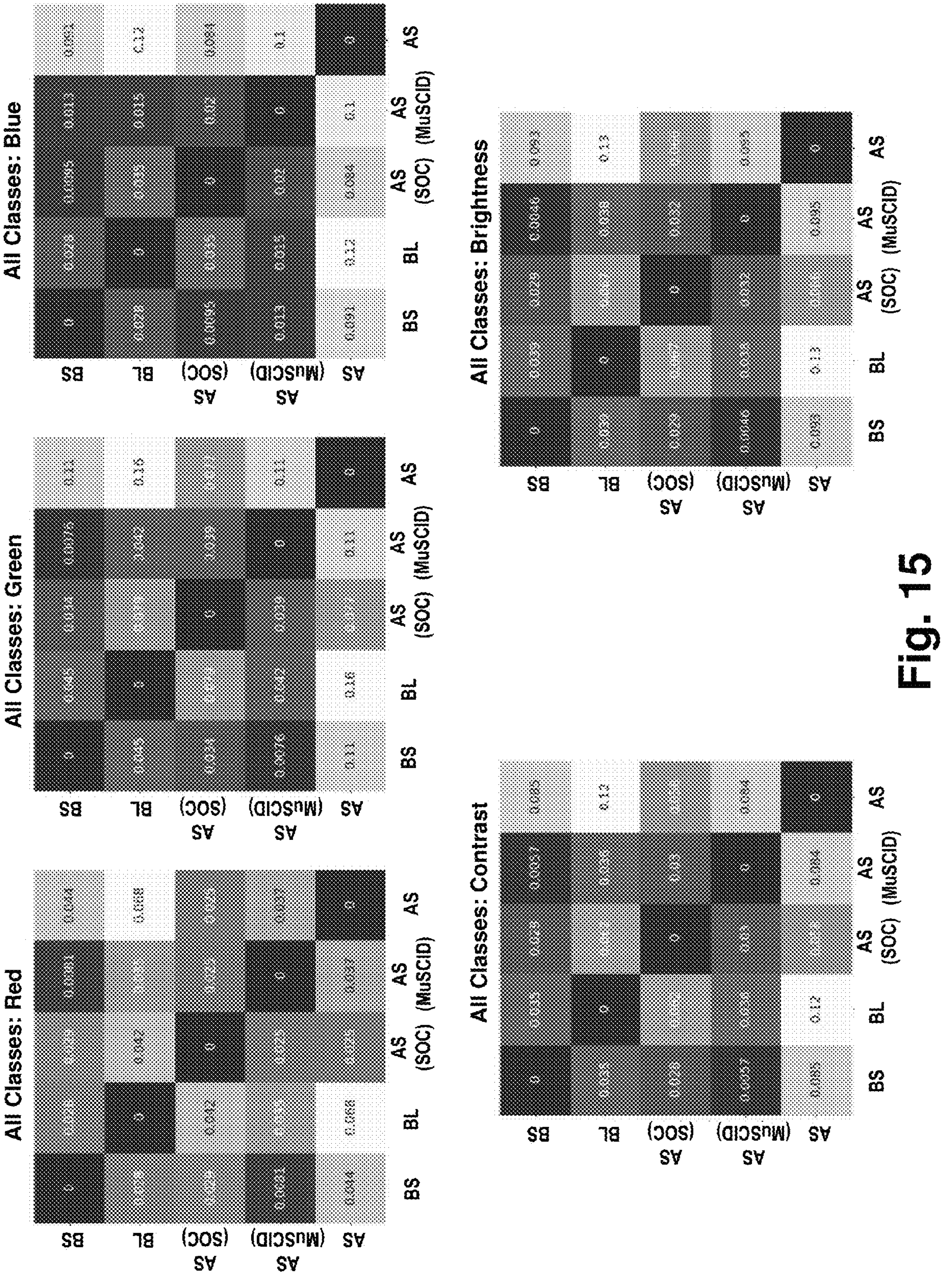
FIGS. 15, 16A, 16B, and 16C show exemplary Wasserstein distances corresponding to different measurements between imaging data sets.

FIG. 10, Table 6, and FIG. 15 show that post-calibration, the distribution of color metrics in $$A_S^L \text{ and } A_S^S$$

are closer to $B_S$ and $B_L$ compared to $A_S$, especially in terms of the green (as much as 69% and 93% closer) and blue channels (85% and 89% closer). This suggest that the calibration indeed dampened the domain shift in both color channels. FIG. 15 and violin plots in FIG. 100 suggest that $$A_S^L \text{ and } A_S^S$$

are also similar in terms of color metrics, indicating MuSCID might be suitable replacement for same organ calibration (SOC).

Keratinization is a potential explanation for the greater green and blue intensities in the Australian versus the Swiss SCC-Invasive lesions. (See, Table 6).

TABLE 6

Class-wise mean intensity of R/G/B channels of Australian skin tissue before ($A_s$) and after calibration ($A_S^L$ and $A_S^S$) compared to Swiss skin tissue ($B_S$). We highlight the entries where a significant change in intensity values after calibration was observed, resulting in greater similarity between the Australian and Swiss site images.

| | | $A_S$ | $A_S^L$ | $B_S$ | $A_S^S$ |
|---|---|---|---|---|---|
| Benign | R | 0.86 ± 0.05 | 0.86 ± 0.03 | 0.87 ± 0.03 | 0.87 ± 0.04 |
| | G | 0.69 ± 0.08 | **0.76 ± 0.05** | **0.77 ± 0.05** | **0.75 ± 0.07** |

TABLE 6-continued

Class-wise mean intensity of R/G/B channels of Australian skin tissue before ($A_s$) and after calibration ($A_S^L$ and $A_S^S$) compared to Swiss skin tissue ($B_S$). We highlight the entries where a significant change in intensity values after calibration was observed, resulting in greater similarity between the Australian and Swiss site images.

| | | $A_S$ | $A_S^L$ | $B_S$ | $A_S^S$ |
|---|---|---|---|---|---|
| | B | 0.81 ± 0.04 | **0.89 ± 0.02** | **0.86 ± 0.02** | **0.88 ± 0.03** |
| BCC | R | 0.73 ± 0.06 | **0.78 ± 0.02** | **0.84 ± 0.04** | 0.74 ± 0.06 |
| | G | 0.57 ± 0.08 | **0.67 ± 0.04** | **0.74 ± 0.06** | **0.61 ± 0.07** |
| | B | 0.74 ± 0.04 | **0.85 ± 0.02** | **0.87 ± 0.02** | **0.83 ± 0.04** |
| SCC-In | R | 0.79 ± 0.01 | **0.82 ± 0.03** | **0.82 ± 0.05** | 0.79 ± 0.05 |
| Situ | G | 0.61 ± 0.08 | **0.71 ± 0.05** | **0.71 ± 0.07** | 0.63 ± 0.08 |
| | B | 0.77 ± 0.04 | **0.87 ± 0.02** | **0.86 ± 0.03** | **0.83 ± 0.04** |
| SCC- | R | 0.85 ± 0.04 | 0.84 ± 0.03 | 0.8. ± 0.0. | 0.86 ± 0.03 |
| Invasive | G | 0.65 ± 0.51 | 0.74 ± 0.04 | 0.70 ± 0.05 | 0.72 ± 0.04 |
| | B | 0.80 ± 0.02 | **0.88 ± 0.01** | **0.85 ± 0.03** | **0.87 ± 0.01** |

Figure 13:
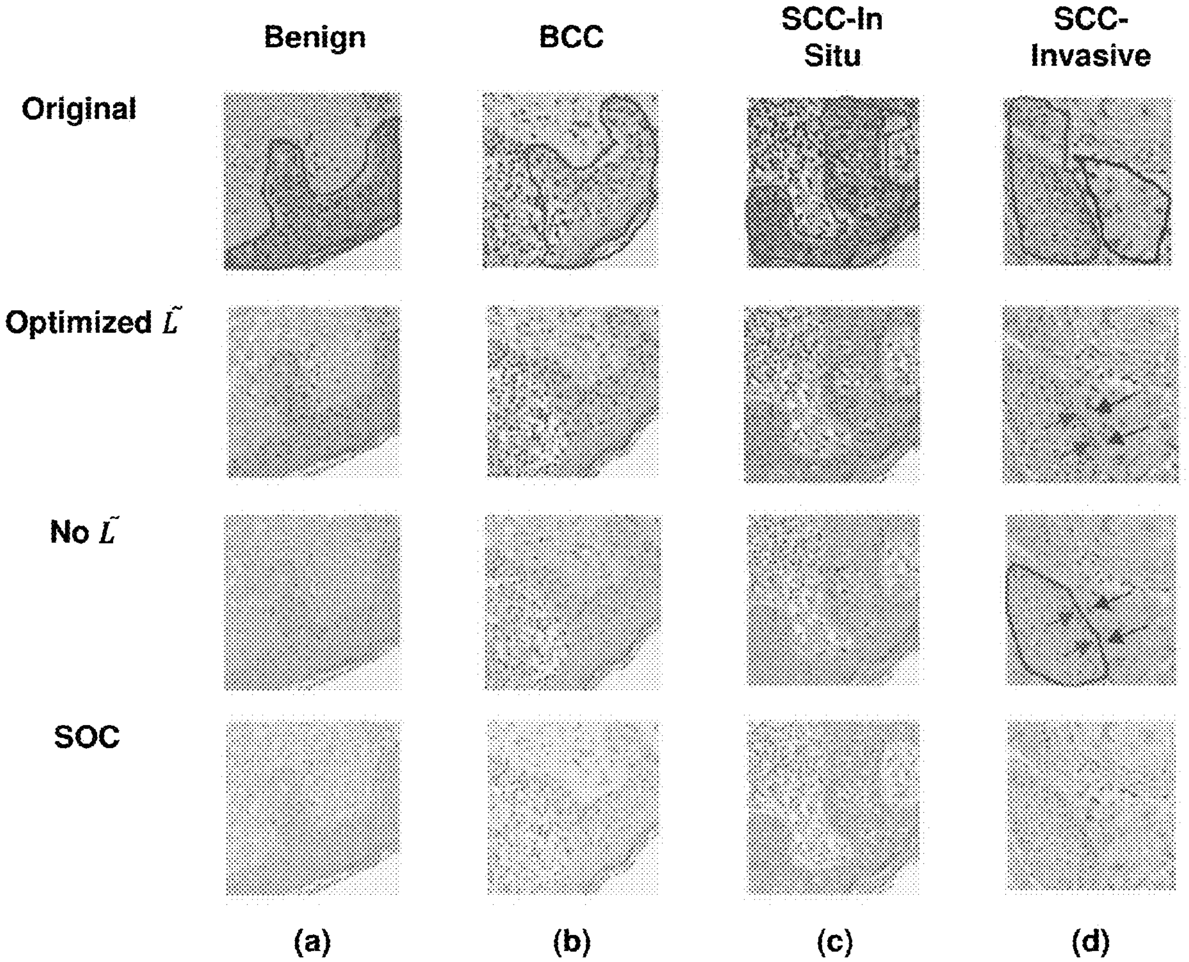
FIG. 13 shows exemplary images showing the effects of domain shift calibration with and without optimizing a loss function.

When the objective reconstruction loss $\tilde{L}$ is minimized during training, the final averaged value of reconstruction loss $\tilde{L}$ across all pairs of images in $$A_S^L a$$

and $A_S$ was 0.076±0.02, versus 0.085±0.025 when reconstruction loss $\tilde{L}$ is not minimized. This 11% quantitative improvement appears to coincide with an improvement in the consistency of skin histology components (see FIG. 13). For example, when not minimizing reconstruction loss $\tilde{L}$, epidermis regions presented in $A_S$ typically have darker colors compared to the dermis regions. With the optimization of reconstruction loss $\tilde{L}$, the epidermis (circled in green) in calibrated outputs of FIG. 13, columns (a) and (c) are of similar color to the remaining dermis regions (circled in red). FIG. 13, column (d) shows that, without reconstruction loss $\tilde{L}$, epidermis region color (green arrows) more closely resembles that of the dermis region (red arrows). During the inspection of the ROIs by the dermatopathologist, skin histologic features were appropriately preserved, with no lung-specific histology being introduced into the calibrated skin tissue. In additional calibration examples, subtle changes in tissue texture details (e.g., nuclei textures) between MuSCID and SOC are highlighted. Importantly, these changes were inspected by the dermatologist, and nothing unreasonable was identified from a biological standpoint, suggesting MuSCID is appropriate for color calibration.

As shown by the Wilcoxon Rank-sum test p-values, morphological feature distributions between $$A_S, A_S^S, A_S^L, B_L$$

and $B_S$ are all significantly different from each other. Ideally, however, morphological differences between $$A_S, A_S^S, \text{and } A_S^L$$

should not be statistically significant, since they contain the same images exposed to different sets of pre-analytic variations. This indicates CycleGAN may transmit different morphological features from templates images ($B_L$ or $B_S$) to $A_S$. To evaluate if such transmission is related to data leakage, more fine-grained comparisons were performed.

First, all Wasserstein distance calculations between skin tissue datasets $$(A_S, A_S^S, A_S^L, \text{and } B_S)$$

are notably smaller as compared to $B_L$, an expected finding given that skin and lung cells present differently. For instance, in terms of the mean nuclei area in FIG. 16A (a), the Wasserstein distance from $$A_S^L$$

to $A_S$ is 71.686, which is about 75% smaller as compared to $B_L$ (291.082). This quantitatively supports the dermatopathologist's visual findings with respect to the similarity of uncalibrated and calibrated skin tissue images, suggesting that both SOC and MuSCID preserve morphological patterns that are specific to the skin.

Further, these results support the notion that SOC may transmit skin-specific morphological information from $B_S$ into $$A_S^S.$$

Figure 16A:
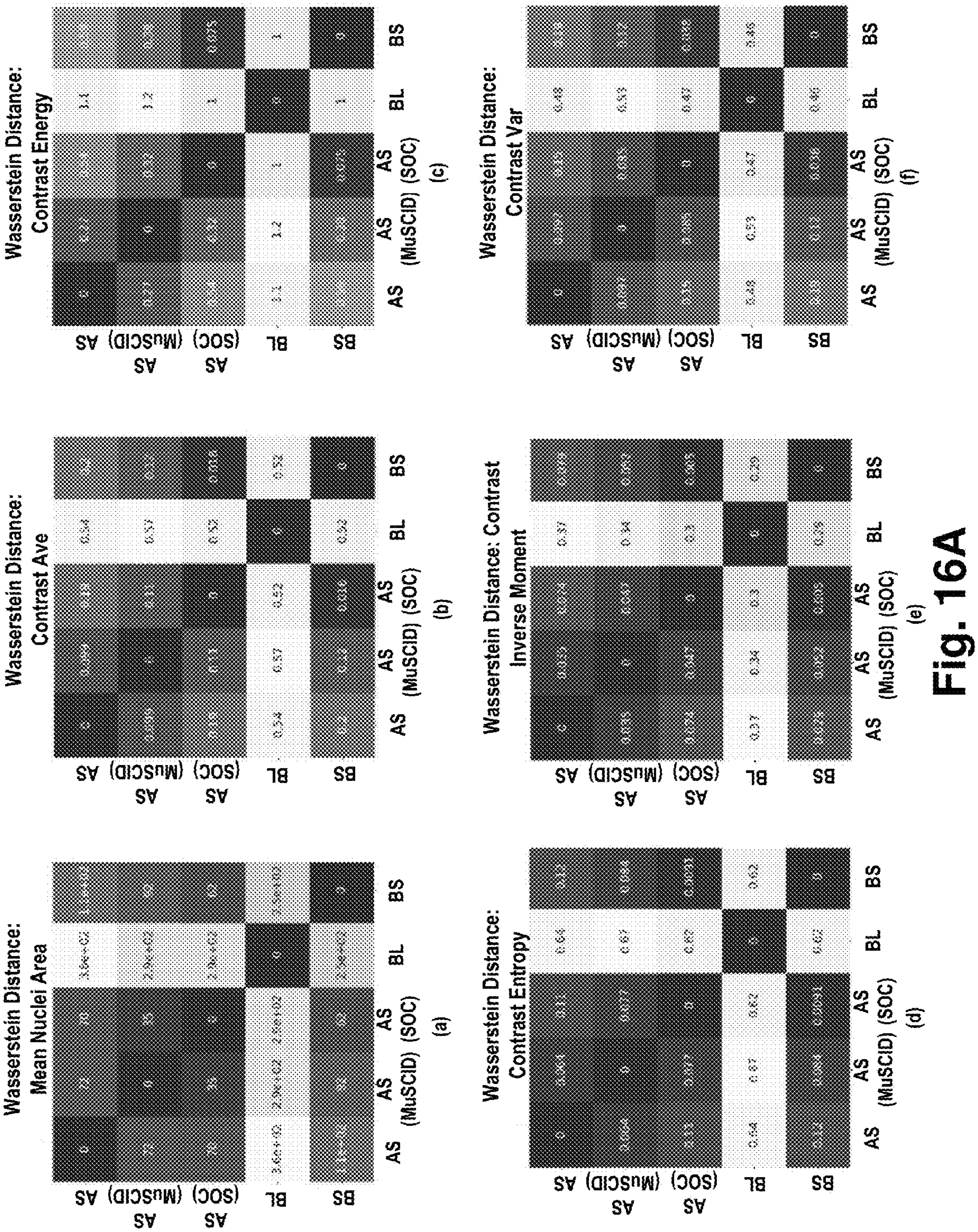
Figure 16B:
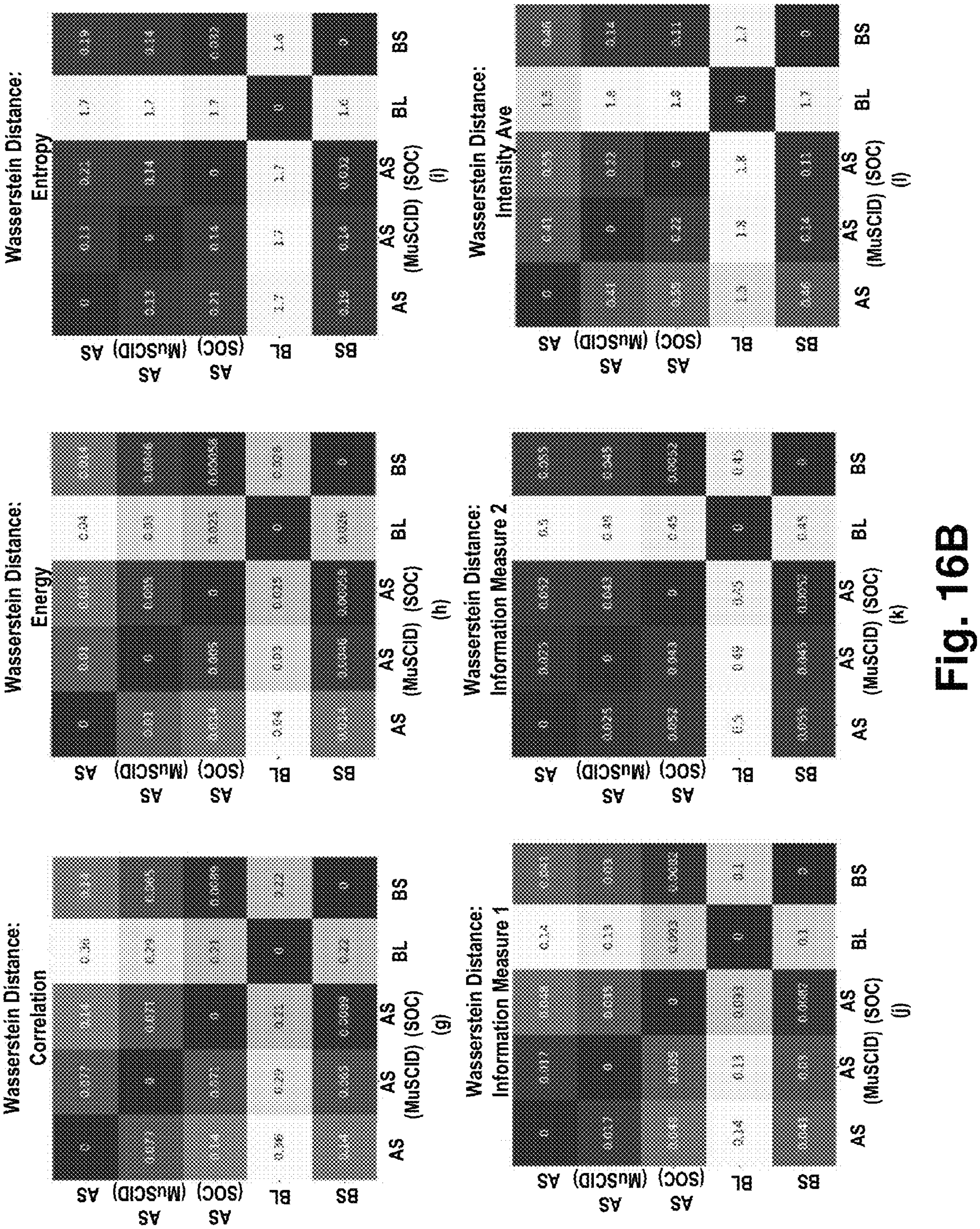
Figure 16C:
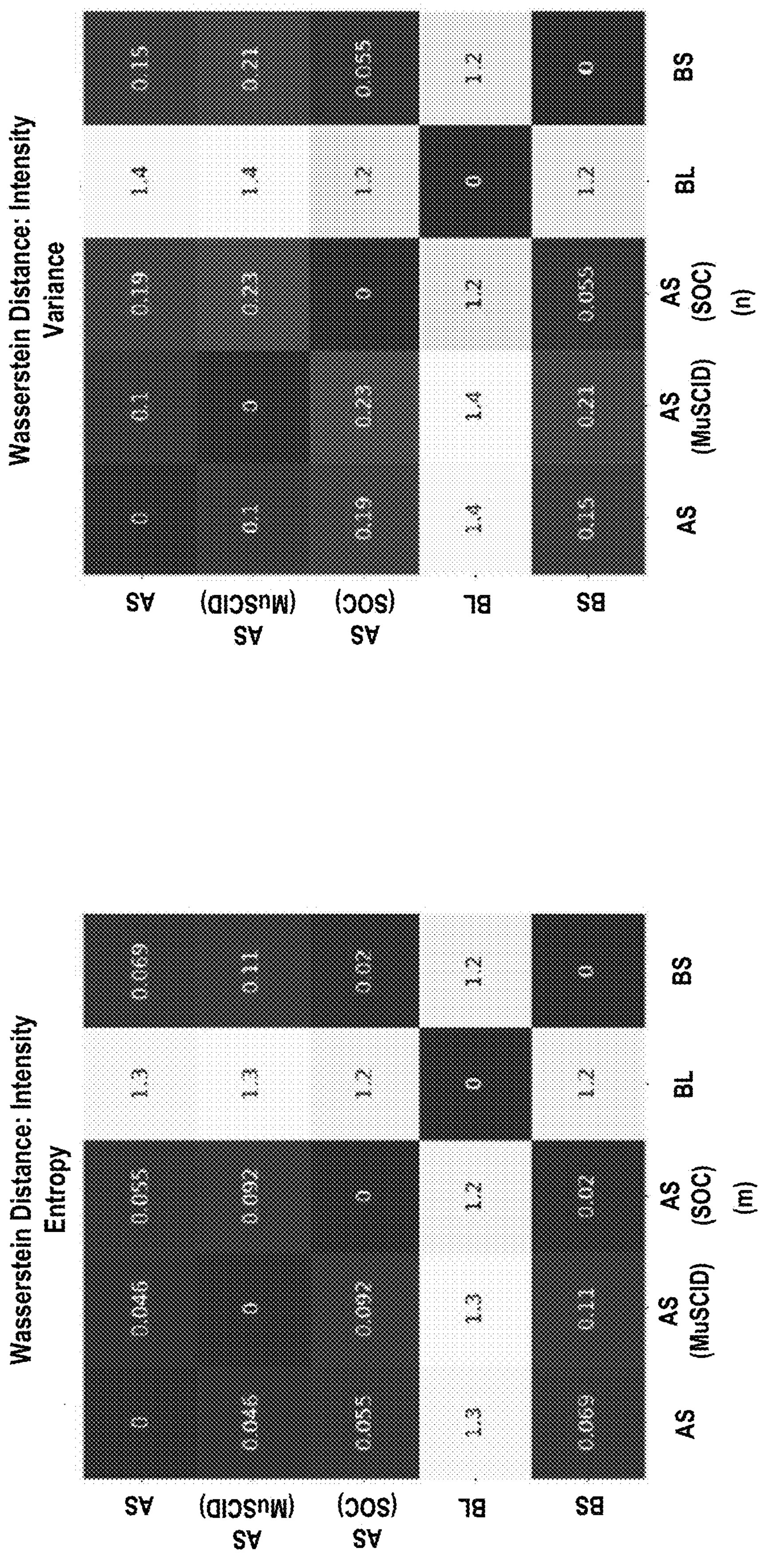

For example, FIGS. 16A-16C (a) to (n), shows the distance between $$A_S^S$$

and $B_S$ being smaller than that between $$A_S^L$$

to $B_S$, with a mean nuclei size of $$A_S^S$$

31% closer to $B_S$ (distance 62.094) compared to from $$A_S^L$$

to $B_S$ (distance 91.545). This smaller distance suggests the presence of data leakage in SOC from $B_S$ templates.

Taken together, these findings suggest that potential data leakage in SOC use cases may not be adequately ruled out, motivating the need for off-target normalization processes like MuSCID. Examining Wasserstein distances between $B_L$ and $B_S$, reveals the least amount of shared morphological information. This further provides evidence that the risk of data leakage in MuSCID is minimized due to organ-specific information being unavailable for transmission from the onset. Moreover, $A_S^L$ reasonably preserves skin morphological features, in turn suggesting that MuSCID is an appropriate surrogate to SOC.

Experiment 2 Results and Discussion: Comparative Evaluation of MC and MN in Terms of AUC for NMSC Diagnosis and Classification The similarity in AUC between $$E_{A_S^L, A_S^L} \text{ and } E_{A_S, A_S}$$

suggest minimal error is introduced into the training data $D_T$ during the calibration process. (See, Table 7). On the other hand, differences in AUC were witnessed when comparing $$E_{A_S, A_S^L}$$

to $E_{A_S,A_S}$, suggesting that the domain shift between $A_S$ and $$A_S^L$$

in testing data $D_V$ is sufficient to degrade the performance of the NSMC-subtyping model. Conversely, when a downstream classification model trained with calibrated data ($M_c$) was employed on $$AS\ E_{A_S^L, A_S} \text{ vs. } E_{A_S^L, A_S^L},$$

diminished performance was again observed, as evidenced by patch-level AUCs. Taken together, these results support our hypothesis that domain shift degrades the performance of DL-based NMSC-subtyping models. Corresponding ROC curves of the AUC values in Table 7 are illustrated in Section S2.9.

TABLE 7

| Patch-level AUCs | Benign | BCC | SCC-In Situ | SCC-Invasive |
|---|---|---|---|---|
| $E_{A_S,A_S}$ | 0.99 | 0.99 | 0.97 | 0.99 |
| $E_{A_S^L,A_S^L}$ | 0.98 | 0.99 | 0.94 | 0.98 |
| $E_{A_S,A_S^L}$ | 0.98 | 0.91 | 0.76 | 0.97 |
| $E_{A_S^L,A_S}$ | 0.98 | 0.96 | 0.80 | 0.95 |
| $E_{A_S^S,A_S^S}$ | 0.98 | 0.99 | 0.92 | 0.86 |
| $E_{A_S,A_S}$ | 0.97 | 0.98 | 0.92 | 0.97 |
| $E_{A_S^L,A_S^L}$ | 0.96 | 0.97 | 0.91 | 0.98 |
| $E_{A_S,A_S^L}$ | 0.99 | 0.94 | 0.78 | 0.91 |
| $E_{A_S^L,A_S}$ | 0.97 | 0.96 | 0.88 | 0.99 |
| $E_{A_S^S,A_S^S}$ | 0.90 | 0.95 | 0.85 | 0.94 |

(a) Patch-level and (b) Patient-level one-vs.-rest multiclass AUC of comparison strategies for the training and internal validation.
The AUC of $E_{A_S A_S}$ close to +L6$E_{A_S^L,A_S^L}$
indicating only limited error was introduced in DT by MuSCID, which may otherwise potentially degrade the model performance.

Next, to demonstrate that MuSCID aids in mitigating the domain shift between Australian and Swiss skin tissue images, AUC values between $$E_{A_S^L, B_S} \text{ and } E_{A_S, B_S}$$

were compared and found to be statistically significant for the subtyping of BCC and SCC-Invasive classification problems. (See, Table 8). While an improvement in AUC of almost 14% was observed after calibration, the improvement was not found to be statistically significant for SCC-In Situ cases (p=0.15), likely due to the limited sample size (n=9 for benign and n=12 for SCC-n Situ). Comparing $$E_{A_S^S, B_S} \text{ to } E_{A_S^L, B_S}$$

resulted in a statistically significant improvement only for the SCC-Invasive cases, with a 3% larger AUC value. This appears to suggest that MuSCID and SOC are similar in their performance of mitigating domain shift. Hence, MuSCID appears to be a suitable replacement for the more commonly employed SOC approaches, with the added benefit of further minimizing the risk of data leakage.

TABLE 8

| Patient-level AUCs | Benign (p-0.47) | BCC (p-0.01) | SCC-In Situ (p-0.15) | SCC-Invasive (p-1e-5) |
|---|---|---|---|---|
| $E_{A_S^L,B_S}$ | 0.92 | 0.92 | 0.87 | 0.92 |
| $E_{A_S,B_S}$ | 0.96 | 0.87 | 0.73 | 0.82 |

| $E_{A_S^S,B_S}$ | AUC | p-value $(vs.\ E_{A_S^L,B_S})$ |
|---|---|---|
| Benign | 0.98 | 0.40 |
| BCC | 0.95 | 0.052 |
| SCC-In Situ | 0.85 | 0.84 |
| SCC-Invasive | 0.95 | 0.03 |

(a) Held-out test of the ResNext50_32xD NMSC-subtyping model with and without calibrating the DT using lung tissue templates from the testing site. (b) The held-out test result from the SOC counterparts and the corresponding Delong test p-value against the MuSCID.

We highlighted the statistically significant p-value (SCC-Invasive), suggesting that the performance of the NMSC-subtyping between SOC and MuSCID is significantly different only in the SCC-Invasive cases, with a 3% difference in AUC scores. The performance between SOC and MuSCID in regards to the AUC of NMSC0subtyping are similar in benign, BCC, and SCC-In Situ.

Figure 14:
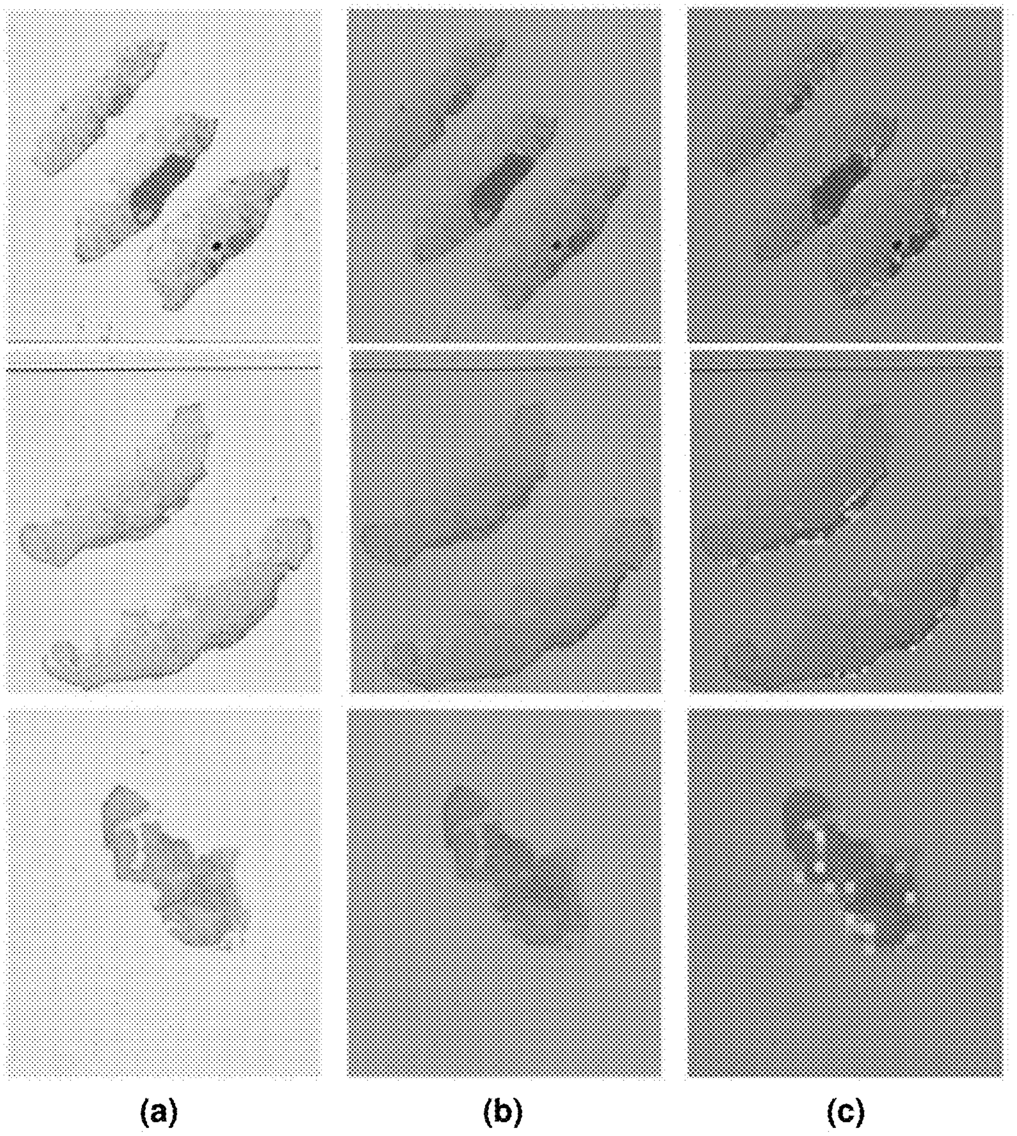
FIG. 14 shows exemplary WSI level saliency maps produced using a NMSC diagnosis system on a data set including images of skin tissue calibrated with lung tissue.

In addition to quantitative evaluation, a qualitative heatmap visualization of regions identified as BCC/SCC-In Situ/SCC-Invasive was also provided. (See, FIG. 14). The NMSC-subtyping model appears to adequately capture the cancerous regions. False positives, especially in SCC cases, do exist in certain regions due to the sectioning of the specimen and the lack of context.

CONCLUSION

In this example use case, we presented Multi-Site Cross-Organ Calibrated Deep Learning (MuSCID), a new approach to mitigate a domain shift between multiple sites and applied it to non-melanoma skin cancer (NMSC) subtyping use case. MuSCID appears to effectively mitigate domain shift across histopathological images from different sites, aiding in the quest for increased generalizability of DL-based computational pathology approaches. Specifically in this example use case, MuSCID was found to aid in the identification of cases of benign, basal cell carcinoma (BCC), in situ squamous cell carcinoma (SCC-In Situ), and invasive squamous cell carcinoma (SCC-Invasive). We evaluated the performance of MuSCID by (1) assessing changes in color-based image metrics pre- and post-calibration of training images; (2) examining the improved generalizability of the NMSC-subtyping model across sites afforded by calibration; (3) comparing the color distribution and held-out test AUC score of MuSCID to the SOC. We show that cross-organ calibration can aid in mitigating domain shift while mitigating the risk of data leakage. To the best of our knowledge, this multi-site NMSC-subtyping study is the largest to date, involving over 400 patients (n=437) curated from two international institutions.

Our study demonstrates that MuSCID performs comparably to more common SOC approaches both qualitatively and quantitively, and thus may be able to act as a SOC replacement that minimizes data leakage risk. Notably, our approach modifies training data $D_T$ in the calibration procedure, mitigating the likelihood of artifact introduction into testing data $D_V$. Interestingly, we show that employing cross-organ calibration does not affect the underlying histologic fidelity of the training data $D_T$. Specifically, this study shows that lung tissue can be employed for the calibration of skin tissue, and further aids in mitigating the decrease in performance due to domain shift of an NMSC-subtyping model.

Previous methods of NMSC-subtyping suffer from domain shift. Here when employing MuSCID, the performance of a DL-based NMSC-subtyping was on par with previous intra-site studies, while also mitigating the effects of domain shift in cross-site evaluation. Moreover, NMSC classification problems may be increased by the inclusion of SCC-In Situ disease.

Overall, this example use case shows that MuSCID successfully mitigates the domain shift between two sites of skin data by employing off-target organ calibration. Data calibrated with MuSCID showed improved subsequent cross-site NMSC-subtyping performance, while minimizing the potential risk of data leakage.

Therefore, the present disclosure relates to a method and associated apparatus for using cross-organ calibration to mitigate domain shift batch effects between images having different data acquisition attributes (e.g., due to different acquisition sites). The cross-organ calibration method modifies an on-target organ (e.g., an organ that is used in subsequent machine learning analysis) within a first imaging data set using an off-target organ (e.g., an organ that is not used in subsequent machine learning analysis) within a second imaging data set.

In some embodiments, the present disclosure relates to a method of mitigating domain shift. The method includes accessing a first imaging data set having one or more first images from a first site, the one or more first images respectively including a first on-target region; accessing a second imaging data set having one or more second images from a second site, the one or more second images respectively including a second off-target region; and modifying the first on-target region using the second off-target region to generate a calibrated first on-target region, the calibrated first on-target region having a first domain shift with respect to the second off-target region and the first on-target region has a second domain shift with respect to the first on-target region, the first domain shift being smaller than the second domain shift In other embodiments, the present disclosure relates to a non-transitory computer-readable medium storing computer-executable instructions that, when executed, cause a processor to perform operations, including accessing a first imaging data set having one or more first images of a patient from a first site, the one or more first images respectively including a first on-target organ; accessing a second imaging data set having one or more second images from a second site, the one or more second images respectively including a second off-target organ; modifying the first on-target organ using the second off-target organ to generate a calibrated first on-target organ; and operating upon the calibrated first on-target organ with a machine learning stage to generate a medical prediction concerning the patient In yet other embodiments, the present disclosure relates to an apparatus. The apparatus includes a memory configured to store a first imaging data set having one or more first images from a first site and a second imaging data set having one or more second images from a second site, the one or more first images respectively include a first on-target organ and the one or more second images respectively include a second off-target organ; and a domain shift calibrator configured to modify the first on-target organ using the second off-target organ to generate a calibrated first on-target organ, the calibrated first on-target organ having a first domain shift with respect to the second off-target organ and the first on-target organ having a second domain shift with respect to the second off-target organ, the first domain shift being smaller than the second domain shift.

Examples herein can include subject matter such as an apparatus, including a digital whole slide scanner, a CT system, an MRI system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system according to embodiments and examples described. References to “one embodiment”, “an embodiment”, “one example”, and “an example” indicate that the embodiment(s) or example(s) so described may include a particular feature, structure, characteristic, property, element, or limitation, but that not every embodiment or example necessarily includes that particular feature, structure, characteristic, property, element or limitation.

Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action (s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A method of mitigating domain shift, comprising:

accessing a first imaging data set comprising one or more first images from a first site, wherein the one or more first images respectively comprise a first on-target region;

accessing a second imaging data set comprising one or more second images from a second site, wherein the one or more second images respectively comprise a second off-target region; and modifying the first on-target region using the second off-target region to generate a calibrated first on-target region, wherein the calibrated first on-target region has a first domain shift with respect to the second off-target region and the first on-target region has a second domain shift with respect to the first on-target region, the first domain shift being smaller than the second domain shift.

2. The method of claim 1, further comprising:

applying a deep learning model to the calibrated first on-target region during training, wherein the deep learning model is configured to classify the first on-target region as cancerous or benign.

3. The method of claim 2, wherein the first on-target region comprises skin tissue; and wherein the second off-target region comprises lung tissue.

4. The method of claim 3, wherein the deep learning model is configured to distinguish between squamous cell carcinomas (SCC) subtypes including SCC-in Situ and SCC-Invasive.

5. The method of claim 1, wherein the first on-target region comprises tissue from a first on-target organ and the second off-target region comprises tissue from a second off-target organ that is different than the first on-target organ.

6. The method of claim 1, wherein the second imaging data set further comprises a second on-target region; and wherein a deep learning model is trained using the calibrated first on-target region and the second on-target region.

7. The method of claim 1, further comprising:

accessing an additional image of an additional patient generated at the first site, the additional image having an additional on-target region;

modifying the additional on-target region based on the second off-target region to generate a calibrated additional on-target region; and applying a deep learning model to the calibrated additional on-target region to generate a medical prediction concerning the additional patient.

8. The method of claim 7, wherein the first on-target region is modified to generate the calibrated first on-target region using a trained general adversarial network (GAN); and wherein the additional on-target region is modified to generate the calibrated additional on-target region using the trained GAN.

9. The method of claim 1, wherein the first site is a first geographic location and the second site is a second geographic location that is different than the first geographic location.

10. The method of claim 1, wherein the one or more first images are generated at the first site using a first scanner and the one or more second images are generated at the second site using a second scanner that is different than the first scanner.

11. The method of claim 1, further comprising:

extracting a first plurality of patches from the one or more first images;

extracting a second plurality of patches from the one or more second images;

identifying a first plurality of on-target patches from the first plurality of patches, wherein the first plurality of on-target patches correspond to the first on-target region;

identifying a second plurality of off-target patches from the first plurality of patches, wherein the second plurality of off-target patches correspond to the second off-target region;

modifying one of the first plurality of on-target patch using the second plurality of off-target patches to generate a calibrated first on-target patch;

generating a class prediction score for the calibrated first on-target patch;

forming a histogram by aggregating patch level class prediction scores for different types of cancer;

normalizing and concatenating the histogram to generate a vector; and providing the vector to a machine learning model to generate a medical prediction of a patient.

12. A non-transitory computer-readable medium storing computer-executable instructions that, when executed, cause a processor to perform operations, comprising:

accessing a first imaging data set comprising one or more first images of a patient from a first site, wherein the one or more first images respectively comprise a first on-target organ;

accessing a second imaging data set comprising one or more second images from a second site, wherein the one or more second images respectively comprise a second off-target organ;

modifying the first on-target organ using the second off-target organ to generate a calibrated first on-target organ; and operating upon the calibrated first on-target organ with a machine learning stage to generate a medical prediction concerning the patient.

13. The non-transitory computer-readable medium of claim 12, wherein the second off-target organ resembles the first on-target organ in terms of tissue type, stain, or composition of tissue histologic structures.

14. The non-transitory computer-readable medium of claim 12, wherein the second imaging data set further comprises a second on-target organ; and wherein the machine learning stage is trained using the calibrated first on-target organ.

15. The non-transitory computer-readable medium of claim 12, wherein the first site is a first geographic location and the second site is a second geographic location that is different than the first geographic location.

16. An apparatus, comprising:

a memory configured to store a first imaging data set comprising one or more first images from a first site and a second imaging data set comprising one or more second images from a second site, wherein the one or more first images respectively comprise a first on-target organ and the one or more second images respectively comprise a second off-target organ; and a domain shift calibrator configured to modify the first on-target organ using the second off-target organ to generate a calibrated first on-target organ, wherein the calibrated first on-target organ has a first domain shift with respect to the second off-target organ and the first on-target organ has a second domain shift with respect to the second off-target organ, the first domain shift being smaller than the second domain shift.

17. The apparatus of claim 16, further comprising:

a machine learning stage configured to generate a medical prediction concerning a patient based on the calibrated first on-target organ.

18. The apparatus of claim 17, wherein the medical prediction is a classification of a type or a sub-type of a cancer.

19. The apparatus of claim 17, wherein the medical prediction is a classification of the first on-target organ as benign, basal cell carcinoma (BCC), in-situ squamous cell carcinoma (SCC), or invasive SCC.

20. The apparatus of claim 17, wherein the domain shift calibrator comprises a general adversarial network (GAN) and the machine learning stage comprises a deep learning model.

* * * * *